(12) United States Patent
Kato et al.

(10) Patent No.: US 11,886,113 B2
(45) Date of Patent: Jan. 30, 2024

(54) ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

(71) Applicant: FUJIFILM Corporation, Tokyo (JP)

(72) Inventors: Keita Kato, Haibara-gun (JP);
Michihiro Shirakawa, Haibara-gun (JP); Akiyoshi Goto, Haibara-gun (JP);
Takashi Kawashima, Haibara-gun (JP);
Masafumi Kojima, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 718 days.

(21) Appl. No.: 17/002,911

(22) Filed: Aug. 26, 2020

(65) Prior Publication Data

US 2020/0393756 A1 Dec. 17, 2020

Related U.S. Application Data

(63) Continuation of application No. PCT/JP2019/004129, filed on Feb. 6, 2019.

(30) Foreign Application Priority Data

Mar. 1, 2018 (JP) ................................. 2018-036843

(51) Int. Cl.
| | | |
|---|---|---|
| *G03F 7/004* | (2006.01) | |
| *C07C 381/12* | (2006.01) | |
| *C07D 295/26* | (2006.01) | |
| *C07D 327/08* | (2006.01) | |
| *C07D 333/46* | (2006.01) | |
| *C08L 25/06* | (2006.01) | |
| *C08L 33/06* | (2006.01) | |
| *C08L 33/08* | (2006.01) | |
| *C08L 33/16* | (2006.01) | |
| *G03F 7/115* | (2006.01) | |
| *G03F 7/20* | (2006.01) | |

(52) U.S. Cl.
CPC .......... *G03F 7/0045* (2013.01); *C07C 381/12* (2013.01); *C07D 295/26* (2013.01); *C07D 327/08* (2013.01); *C07D 333/46* (2013.01); *C08L 25/06* (2013.01); *C08L 33/064* (2013.01); *C08L 33/08* (2013.01); *C08L 33/16* (2013.01); *G03F 7/115* (2013.01); *G03F 7/2053* (2013.01)

(58) Field of Classification Search
CPC .. C07C 381/12; C07D 291/00; C07D 291/02; C07D 291/04; C07D 291/06
See application file for complete search history.

(56) References Cited

U.S. PATENT DOCUMENTS

| | | | | |
|---|---|---|---|---|
| 10,042,251 | B2* | 8/2018 | LaBeaume | ........... C07D 333/76 |
| 10,173,975 | B2* | 1/2019 | Ohashi | .................. G03F 7/0397 |
| 10,248,022 | B2* | 4/2019 | Ohashi | .................. G03F 7/0046 |
| 11,067,890 | B2* | 7/2021 | Goto | ...................... G03F 7/0046 |
| 2015/0004544 | A1* | 1/2015 | Namai | .................. G03F 7/2041 |
| | | | | 546/203 |
| 2015/0301451 | A1 | 10/2015 | Iwato | |
| 2016/0070167 | A1* | 3/2016 | Kataoka | ................ C08F 220/26 |
| | | | | 430/311 |
| 2016/0349612 | A1* | 12/2016 | Fujiwara | .............. C07D 335/16 |
| 2020/0012189 | A1 | 1/2020 | Goto et al. | |
| 2020/0071268 | A1* | 3/2020 | Inoue | .................... G03F 7/0046 |

FOREIGN PATENT DOCUMENTS

| | | |
|---|---|---|
| JP | 2013-167825 A | 8/2013 |
| JP | 2014-170205 A | 9/2014 |
| JP | 2014-199389 A | 10/2014 |
| JP | 2016-222549 A | 12/2016 |

(Continued)

OTHER PUBLICATIONS

Office Action dated Oct. 14, 2022 issued by the Taiwanese Patent Office in Taiwanese Application No. 108106125.
Office Action dated Aug. 17, 2021 in Japanese Application No. 2020-502899.
International Search Report dated Apr. 9, 2019 from the International Searching Authority in International Application No. PCT/JP2019/004129.
Written Opinion dated Apr. 9, 2019 from the International Bureau in International Application No. PCT/JP2019/004129.

(Continued)

*Primary Examiner* — Amanda C. Walke
(74) *Attorney, Agent, or Firm* — Sughrue Mion, PLLC

(57) ABSTRACT

The present invention provides an actinic ray-sensitive or radiation-sensitive resin composition with which a pattern having an excellent pattern collapse suppressing property and excellent LWR performance can be obtained. In addition, the present invention also provides a resist film, a pattern forming method, and a method for manufacturing an electronic device, each regarding the actinic ray-sensitive or radiation-sensitive resin composition. The actinic ray-sensitive or radiation-sensitive resin composition of the present invention includes a resin whose solubility in a developer is changed by the action of an acid, a photoacid generator represented by General Formula (b1), and a solvent, in which the photoacid generator represented by General Formula (b1) is a compound that generates an acid having a pka of 1.0 or less upon irradiation with actinic rays or radiation (b1)

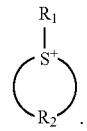

15 Claims, No Drawings

(56) References Cited

FOREIGN PATENT DOCUMENTS

TW    201708188 A    3/2017
WO    2018168260 A1  9/2018

OTHER PUBLICATIONS

International Preliminary Report on Patentability dated Sep. 1, 2020 from the International Bureau in International Application No. PCT/JP2019/004129.
Notification of Reason for Refusal dated May 6, 2022 from the Korean Patent Office in Korean Application No. 10-2020-7024722.

* cited by examiner

ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

CROSS-REFERENCE TO RELATED APPLICATIONS

This application is a Continuation of PCT International Application No. PCT/JP2019/004129 filed on Feb. 6, 2019, which claims priority under 35 U.S.C. § 119(a) to Japanese Patent Application No. 2018-036843 filed on Mar. 1, 2018. The above application is hereby expressly incorporated by reference, in its entirety, into the present application.

BACKGROUND OF THE INVENTION

1. Field of the Invention

The present invention relates to an actinic ray-sensitive or radiation-sensitive resin composition, a resist film, a pattern forming method, and a method for manufacturing an electronic device.

2. Description of the Related Art

Since the advent of a resist for KrF excimer laser (248 nm), a pattern forming method utilizing chemical amplification is used in order to compensate for a decrease in sensitivity due to light absorption. For example, in a positive tone chemical amplification method, first, a photoacid generator included in the exposed portion decomposes upon irradiation with light to generate an acid. Then, in a post-exposure baking step and the like, a solubility in a developer is changed by changing an alkali-insoluble group contained in a resin included in an actinic ray-sensitive or radiation-sensitive resin composition to an alkali-soluble group by the catalytic action of an acid thus generated. Thereafter, development is performed using, for example, an organic solvent. As a result, the unexposed portion is removed to obtain a desired pattern.

In order to make semiconductor elements finer, the wavelength of an exposure light source has been shortened and a projection lens with a high numerical aperture (high NA) has been advanced, and an exposure machine using an ArF excimer laser having a wavelength of 193 nm as a light source is currently being developed.

Under these circumstances, various configurations have been proposed as actinic ray-sensitive or radiation-sensitive resin compositions.

For example, JP2016-222549A discloses a chemically amplified resist composition including a photoacid generator consisting of a sulfonium salt represented by the following formula.

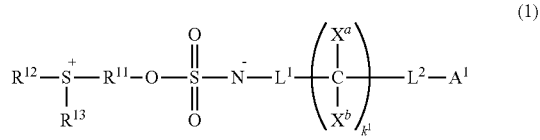

(1)

SUMMARY OF THE INVENTION

The present inventors have specifically examined the compound disclosed in JP2016-222549A, and as a result, they have found that there is room for improvement in the performance of suppressing pattern collapse (hereinafter also referred to as a "pattern collapse suppressing property") in formation of a pattern and the line width roughness (LWR) performance of the obtained pattern with an actinic ray-sensitive or radiation-sensitive resin composition using the compound disclosed in JP2016-222549A.

Therefore, it is an object of the present invention to provide an actinic ray-sensitive or radiation-sensitive resin composition with which a pattern having an excellent pattern collapse suppressing property and excellent LWR performance can be obtained.

In addition, another object of the present invention is to provide a resist film, a pattern forming method, and a method for manufacturing an electronic device, each regarding the actinic ray-sensitive or radiation-sensitive resin composition.

The present inventors have conducted intensive studies to accomplish the objects, and as a result, they have found that the problems can be solved by using a photoacid generator having a specific structure, and have completed the present invention.

That is, the present inventors have found that the problems can be solved by the following configurations.

[1] An actinic ray-sensitive or radiation-sensitive resin composition comprising:
a resin whose solubility in a developer is changed by the action of an acid; and
a photoacid generator represented by General Formula (b1) which will be described later,
in which the photoacid generator represented by General Formula (b1) which will be described later is a compound that generates an acid having a pka of 1.0 or less upon irradiation with actinic rays or radiation.

[2] The actinic ray-sensitive or radiation-sensitive resin composition as described in in which the anionic group is a group represented by any of General Formulae (b1-1) to (b1-3) which will be described later.

[3] The actinic ray-sensitive or radiation-sensitive resin composition as described in [2],
in which the anionic group is a group represented by General Formula (b1-1) which will be described later or a group represented by General Formula (b1-3) which will be described later.

[4] The actinic ray-sensitive or radiation-sensitive resin composition as described in any one of [1] to [3],
in which the photoacid generator represented by General Formula (b1) which will be described later is a compound represented by General Formula (ZI-3) which will be described later or a compound represented by General Formula (ZI-4) which will be described later.

[5] The actinic ray-sensitive or radiation-sensitive resin composition as described in any one of [1] to [4], further comprising an acid diffusion control agent.

[6] The actinic ray-sensitive or radiation-sensitive resin composition as described in [5],
in which the acid diffusion control agent is a basic compound whose basicity is reduced or lost upon irradiation with actinic rays or radiation, with the compound being different from the photoacid generator represented by General Formula (b1) which will be described later.

[7] The actinic ray-sensitive or radiation-sensitive resin composition as described in [6],
in which the basic compound whose basicity is reduced or lost upon irradiation with actinic rays or radiation is a compound having an anion represented by General Formula (c-1) which will be described later.

[8] The actinic ray-sensitive or radiation-sensitive resin composition as described in [6],
in which a pka of an acid generated by the basic compound whose basicity is reduced or lost upon irradiation with actinic rays or radiation is more than 1.0.

[9] A resist film formed using the actinic ray-sensitive or radiation-sensitive resin composition as described in any one of [1] to [8].

[10] A pattern forming method comprising:
a step of forming a resist film using the actinic ray-sensitive or radiation-sensitive resin composition as described in any one of [1] to [8] on a support;
a step of exposing the resist film; and
a step of developing the exposed resist film using a developer.

[11] A method for manufacturing an electronic device, comprising the pattern forming method as described in [10].

According to the present invention, it is possible to provide an actinic ray-sensitive or radiation-sensitive resin composition with which a pattern having an excellent pattern collapse suppressing property and excellent LWR performance can be obtained.

In addition, another object of the present invention is to provide a resist film, a pattern forming method, and a method for manufacturing an electronic device, each regarding the actinic ray-sensitive or radiation-sensitive resin composition.

DESCRIPTION OF THE PREFERRED EMBODIMENTS

Hereinafter, the present invention will be described in detail.

Description of configuration requirements described below may be made on the basis of representative embodiments of the present invention in some cases, but the present invention is not limited to such embodiments.

In citations for a group (atomic group) in the present specification, in a case where the group is cited without specifying whether it is substituted or unsubstituted, the group includes both a group having no substituent and a group having a substituent. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

"Actinic rays" or "radiation" in the present specification means, for example, a bright line spectrum of a mercury lamp, far ultraviolet rays typified by an excimer laser, extreme ultraviolet rays (EUV light), X-rays, electron beams (EB), or the like. "Light" in the present specification means actinic rays or radiation.

Unless otherwise specified, "exposure" in the present specification encompasses not only exposure by a bright line spectrum of a mercury lamp, far ultraviolet rays typified by an excimer laser, extreme ultraviolet rays, X-rays, EUV light, or the like, but also lithography by particle rays such as electron beams and ion beams.

In the present specification, a numerical range expressed using "to" is used in a meaning of a range that includes the preceding and succeeding numerical values of "to" as the lower limit value and the upper limit value, respectively.

In the present specification, (meth)acrylate represents acrylate and methacrylate.

In the present specification, the weight-average molecular weight (Mw), the number-average molecular weight (Mn), and the dispersity (also referred to as a molecular weight distribution) (Mw/Mn) of a resin are each defined as a value converted in terms of polystyrene by means of gel permeation chromatography (GPC) measurement (solvent: tetrahydrofuran, flow amount (amount of a sample injected): 10 µL, columns: TSK gel Multipore HXL-M manufactured by Tosoh Corporation, column temperature: 40° C., flow rate: 1.0 mL/min, detector: differential refractive index detector) using a GPC apparatus (HLC-8120 GPC manufactured by Tosoh Corporation).

In the present specification, the acid dissociation constant pKa refers to an acid dissociation constant pKa in an aqueous solution, and is defined, for example, in Chemical Handbook (II) (Revised 4th Edition, 1993, compiled by the Chemical Society of Japan, Maruzen Company, Ltd.). A lower value of the acid dissociation constant pKa indicates higher acid strength. Specifically, the acid dissociation constant pKa in an aqueous solution can be actually measured by using an infinite-dilution aqueous solution and measuring the acid dissociation constant at 25° C. Alternatively, the acid dissociation constant pKa can also be determined using the following software package 1 by computation from a value based on a Hammett substituent constant and the database of publicly known literature values. Any of the values of pKa described in the present specification indicate values determined by calculation using the software package.

Software Package 1: Advanced Chemistry Development (ACD/Labs) Software V 8.14 for Solaris (1994-2007 ACD/Labs).

In the present specification, examples of the halogen atom include a fluorine atom, a chlorine atom, a bromine atom, and an iodine atom.

[Actinic Ray-Sensitive or Radiation-Sensitive Resin Composition]

The actinic ray-sensitive or radiation-sensitive resin composition of the embodiment of the present invention (hereinafter also simply referred to as the "composition" or the "composition of the embodiment of the present invention") will be described.

The composition of the embodiment of the present invention is a so-called resist composition, and may be either a positive tone resist composition or a negative tone resist composition. In addition, the composition of the embodiment of the present invention may be either a resist composition for alkali development or a resist composition for organic solvent development.

The composition of the embodiment of the present invention is typically a chemically amplified resist composition.

The composition of the embodiment of the present invention includes a resin whose solubility in a developer changes by the action of an acid (hereinafter also referred to as a "resin A"), a photoacid generator represented by General Formula (b1) which will be described later (hereinafter referred to as a "specific photoacid generator"), and a solvent.

The specific photoacid generator is a photoacid generator that generates an acid with a pka of 1.0 or less upon exposure.

Furthermore, the specific photoacid generator is a compound having a cationic group ($>S^+$—) and an anionic group in the same molecule, in which the cationic group and the anionic group are linked via a covalent bond, and is a so-called betaine compound.

The mechanism by which the objects of the present invention can be accomplished through such a configuration is not always clear, but is presumed as follows by the present inventors.

Since the specific photoacid generator is a betaine compound, it is easy to make the molecular structure of the photoacid generator relatively small. Therefore, it is possible to increase the amount of an acid generated per mass of a photoacid generator, and thus, the fluctuation of the amount of the acid present in the resist film after exposure is small and the dissolution of the resist film in the exposed portion or the unexposed portion in the subsequent developing step proceeds evenly. This is considered to result in an improvement of the pattern collapse suppressing property and the LWR performance of a pattern thus obtained.

<Resin A>

The actinic ray-sensitive or radiation-sensitive resin composition of the embodiment of the present invention contains a resin whose solubility in a developer is changed by the action of an acid (hereinafter also referred to as a "resin A").

The resin A preferably has a repeating unit having a group whose polarity increases through decomposition by the action of an acid (hereinafter also referred to as an "acid-decomposable group").

In this case, in the pattern forming method of an embodiment of the present invention which will be described later, typically, in a case where an alkali developer is adopted as the developer, a positive tone pattern is suitably formed, and in a case where an organic developer is adopted as the developer, a negative tone pattern is suitably formed.

(Repeating Unit Having Acid-Decomposable Group)

The resin A preferably has a repeating unit having an acid-decomposable group.

The acid-decomposable group preferably has a structure in which a polar group is protected with a group that leaves through decomposition by the action of an acid (leaving group).

Examples of the polar group include an acidic group (a group which dissociates in a 2.38%-by-mass aqueous tetramethylammonium hydroxide solution), such as a carboxyl group, a phenolic hydroxyl group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group, and an alcoholic hydroxyl group.

Moreover, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol (for example, a hexafluoroisopropanol group) having the α-position substituted with an electron withdrawing group such as a fluorine atom is excluded as a hydroxyl group. The alcoholic hydroxyl group is preferably a hydroxyl group having an acid dissociation constant (pKa) of 12 to 20.

As the polar group, a carboxyl group, a phenolic hydroxyl group, a fluorinated alcohol group (preferably a hexafluoroisopropanol group), or a sulfonic acid group is preferable.

The group which is preferable as the acid-decomposable group is a group in which a hydrogen atom is substituted with a group (leaving group) that leaves by the action of an acid.

Examples of the group (leaving group) that leaves by the action of an acid include —C($R_{36}$)($R_{37}$)($R_{38}$), —C($R_{36}$)($R_{37}$)(O$R_{39}$), and —C($R_{01}$)($R_{02}$)(O$R_{39}$).

In the formulae, $R_{36}$ to $R_{39}$ each independently an alkyl group, a cycloalkyl group, an aryl group, an aralkyl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, an aralkyl group, or an alkenyl group.

As the alkyl group as each of $R_{36}$ to $R_{39}$, $R_{01}$, and $R_{02}$, an alkyl group having 1 to 8 carbon atoms is preferable, and examples thereof include a methyl group, an ethyl group, a propyl group, an n-butyl group, a sec-butyl group, a hexyl group, and an octyl group.

The cycloalkyl group as each of $R_{36}$ to $R_{39}$, $R_{01}$, and $R_{02}$ may be either a monocycle or polycycle. As the monocycle, a cycloalkyl group having 3 to 8 carbon atoms is preferable, and examples thereof include a cyclopropyl group, a cyclobutyl group, a cyclopentyl group, a cyclohexyl group, and a cyclooctyl group. As the polycycle, a cycloalkyl group having 6 to 20 carbon atoms is preferable, and examples thereof include an adamantyl group, a norbornyl group, an isobornyl group, a camphanyl group, a dicyclopentyl group, an α-pinel group, a tricyclodecanyl group, a tetracyclododecyl group, and an androstanyl group. Further, at least one carbon atom in the cycloalkyl group may be substituted with a heteroatom such as an oxygen atom.

The aryl group as each of $R_{36}$ to $R_{39}$, $R_{01}$, and $R_{02}$ is preferably an aryl group having 6 to 10 carbon atoms, and examples thereof include a phenyl group, a naphthyl group, and an anthryl group.

The aralkyl group as each of $R_{36}$ to $R_{39}$, $R_{01}$, and $R_{02}$ is preferably an aralkyl group having 7 to 12 carbon atoms, and examples thereof include a benzyl group, a phenethyl group, and a naphthylmethyl group.

The alkenyl group as each of $R_{36}$ to $R_{39}$, $R_{01}$, and $R_{02}$ is preferably an alkenyl group having 2 to 8 carbon atoms, and examples thereof include a vinyl group, an allyl group, a butenyl group, and a cyclohexenyl group.

The ring formed by the mutual bonding of $R_{36}$ and $R_{37}$ is preferably a (monocyclic or polycyclic) cycloalkyl group. As the cycloalkyl group, a monocyclic cycloalkyl group such as a cyclopentyl group and a cyclohexyl group, and a polycyclic cycloalkyl group such as a norbornyl group, a tetracyclodecanyl group, a tetracyclododecanyl group, and an adamantyl group are preferable.

The acid-decomposable group preferably has a tertiary alkyl ester group, an acetal group, a cumyl ester group, an enol ester group, or an acetal ester group, and more preferably has the acetal group or the tertiary alkyl ester group.

The resin A preferably has a repeating unit represented by General Formula (AI) as a repeating unit having an acid-decomposable group.

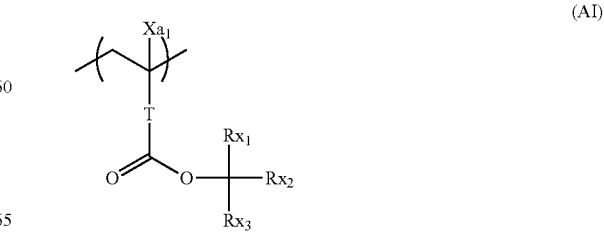

(AI)

In General Formula (AI), T represents a single bond or a divalent linking group.

Examples of the divalent linking group of T include an alkylene group, an arylene group, —COO—Rt-, and —O—Rt-. In the formulae, Rt represents an alkylene group, a cycloalkylene group, or an arylene group.

T is preferably the single bond or —COO—Rt-. Rt is preferably a chained alkylene group having 1 to 5 carbon atoms, and more preferably —$CH_2$—, —$(CH_2)_2$—, or —$(CH_2)_3$—.

T is more preferably a single bond.

In General Formula (AI), $Xa_1$ represents a hydrogen atom, a halogen atom, or a monovalent organic group.

$Xa_1$ is preferably a hydrogen atom or an alkyl group.

The alkyl group of $Xa_1$ may have a substituent, and examples of the substituent include a hydroxyl group and a halogen atom (preferably a fluorine atom).

The alkyl group of $Xa_1$ preferably has 1 to 4 carbon atoms, and examples thereof include a methyl group, an ethyl group, a propyl group, a hydroxymethyl group, and a trifluoromethyl group. The alkyl group of $Xa_1$ is preferably a methyl group.

In General Formula (AI), $Rx_1$ to $Rx_3$ each independently represent an alkyl group or a cycloalkyl group.

Any two of $Rx_1, \ldots,$ or $Rx_3$ may or may not be bonded to each other to form a ring structure.

The alkyl group of each of $Rx_1$, $Rx_2$, and $Rx_3$ may be linear or branched, and is preferably a methyl group, an ethyl group, an n-propyl group, an isopropyl group, an n-butyl group, an isobutyl group, a t-butyl group, or the like. The alkyl group preferably has 1 to 10 carbon atoms, more preferably has 1 to 5 carbon atoms, and still more preferably has 1 to 3 carbon atoms. In the alkyl groups of each of $Rx_1$, $Rx_2$, and $Rx_3$, a part of carbon-carbon bonds may be a double bond.

The cycloalkyl group of each of $Rx_1$, $Rx_2$, and $Rx_3$ may be either a monocycle or a polycycle. Examples of the monocyclic cycloalkyl group include a cyclopentyl group and a cyclohexyl group. Examples of the polycyclic cycloalkyl group include a norbornyl group, a tetracyclodecanyl group, a tetracyclododecanyl group, and an adamantyl group.

A ring formed by the bonding of two of $Rx_1$, $Rx_2$, and $Rx_3$ may be either a monocycle or a polycycle. Examples of the monocycle include monocyclic cycloalkane rings such as a cyclopentyl ring, a cyclohexyl ring, a cycloheptyl ring, and a cyclooctane ring. Examples of the polycycle include polycyclic cycloalkyl rings such as a norbornane ring, a tetracyclodecane ring, a tetracyclododecane ring, and an adamantane ring. Among those, the cyclopentyl ring, the cyclohexyl ring, or the adamantane ring is preferable.

In addition, as a ring formed by the bonding of two of $Rx_1$, $Rx_2$, and $Rx_3$, a ring shown below is also preferable.

Specific examples of the monomer corresponding to the repeating unit represented by General Formula (AI) are shown below. The following specific examples correspond to a case where $Xa_1$ in General Formula (AI) is a methyl group, but $Xa_1$ can be optionally substituted with a hydrogen atom, a halogen atom, or a monovalent organic group.

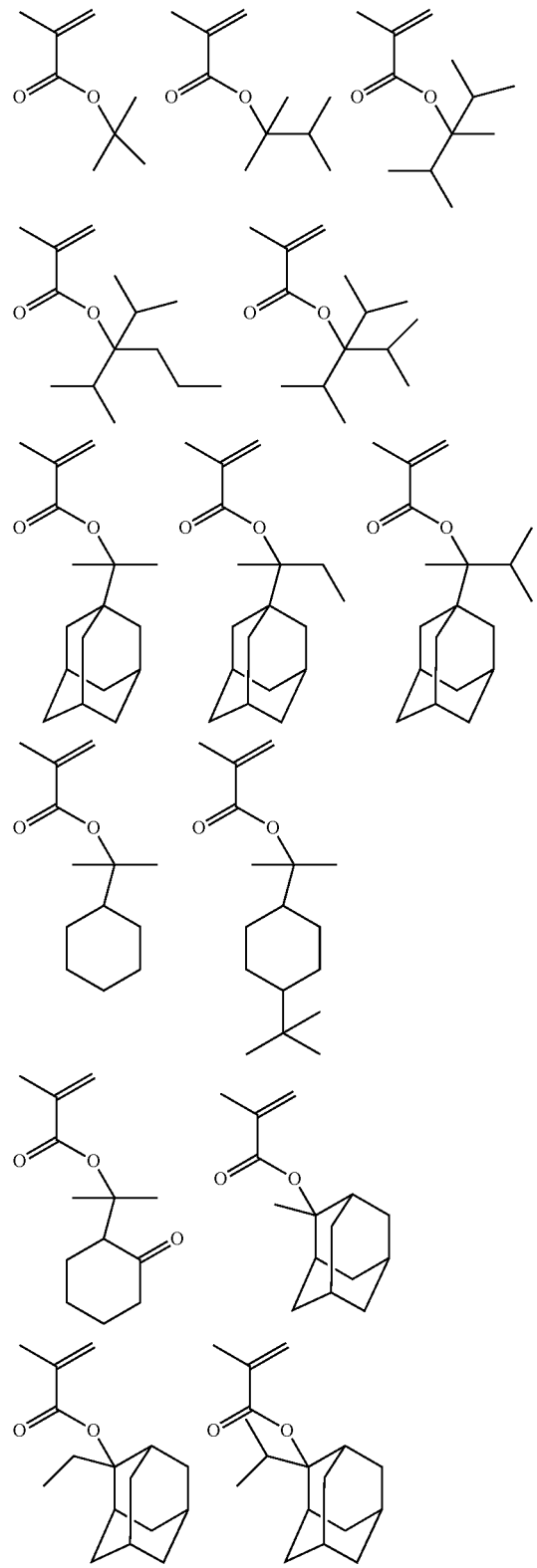

-continued

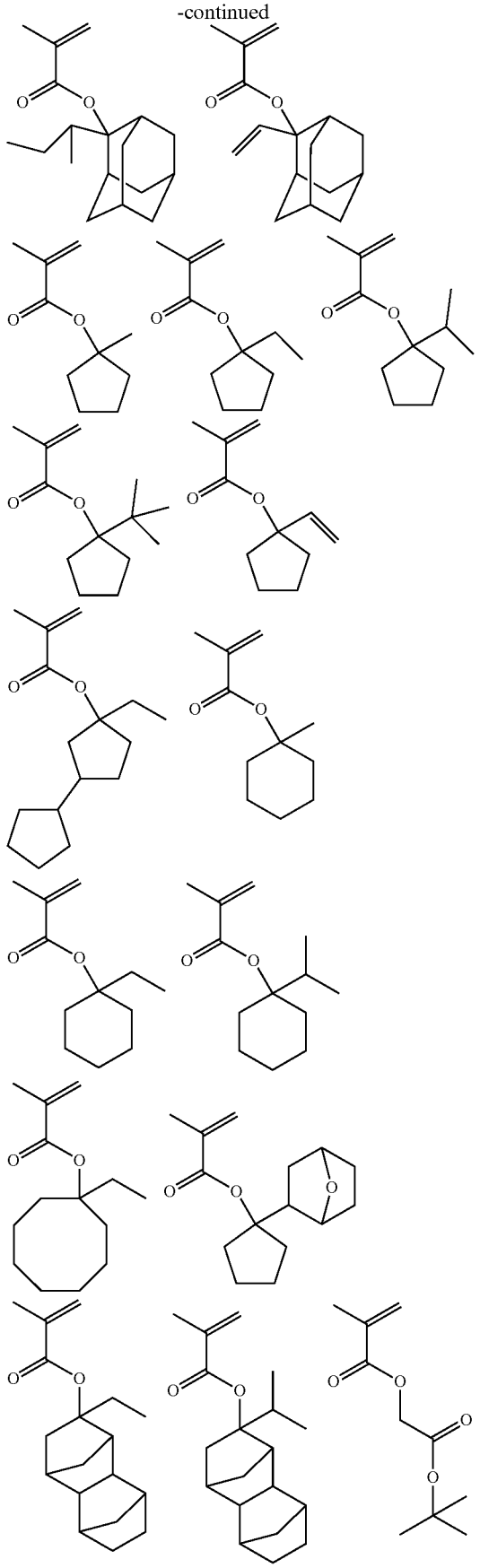

-continued

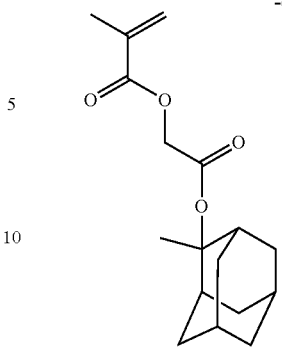

It is also preferable that the resin A has the repeating unit described in paragraphs [0336] to [0369] of the specification of US2016/0070167A1 as the repeating unit having an acid-decomposable group.

Furthermore, the resin A may have a repeating unit including a group that decomposes by the action of an acid to produce an alcoholic hydroxyl group described in paragraphs [0363] to [0364] of the specification of US2016/0070167A1 as a repeating unit having an acid-decomposable group.

The resin A may have the repeating units having an acid-decomposable group singly or in combination of two or more kinds thereof.

A content of the repeating unit having an acid-decomposable group included in the resin A (in a case where the repeating units having an acid-decomposable group are present in a plural number, a total content thereof) is 10% to 90% by mole, more preferably 20% to 80% by mole, and still more preferably 30% to 70% by mole, with respect to all the repeating units of the resin A.

(Repeating Unit Having at Least One Selected from Group Consisting of Lactone Structure, Sultone Structure, and Carbonate Structure)

The resin A preferably has a repeating unit having at least one selected from the group consisting of a lactone structure, a sultone structure, and a carbonate structure.

As the lactone structure or sultone structure, any structure which has a lactone ring or sultone ring may be used, but a lactone structure having a 5- to 7-membered ring or a sultone structure having a 5- to 7-membered ring is preferable.

A lactone structure in which another ring is fused with the 5- to 7-membered lactone ring so as to form a bicyclo structure or a spiro structure is also preferable. A sultone structure in which another ring is fused with a 5- to 7-membered sultone ring so as to form a bicyclo structure or a Spiro structure is also preferable.

Among those, the resin A preferably has a repeating unit having a lactone structure represented by any of General Formulae (LC1-1) to (LC1-22) or a sultone structure represented by any one of General Formulae (SL1-1) to (SL1-3). Further, a lactone structure or sultone structure may be bonded directly to the main chain.

Among those, a lactone structure represented by General Formula (LC1-1), General Formula (LC1-4), General Formula (LC1-5), General Formula (LC1-8), General Formula (LC1-16), General Formula (LC1-21), or General Formula (LC1-22), or a sultone structure represented by General Formula (SL1-1) is preferable.

LC1-1 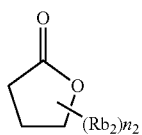
LC1-2 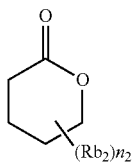
LC1-3 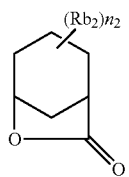
LC1-4 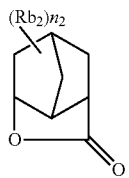
LC1-5 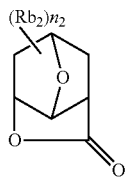
LC1-6 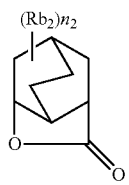
LC1-7 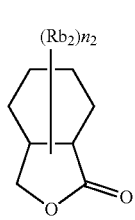
LC1-8 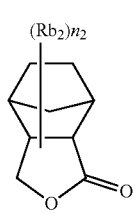
LC1-9 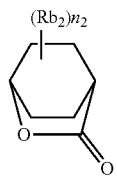
LC1-10 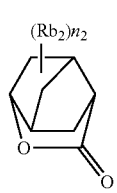
LC1-11 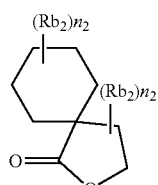
LC1-12 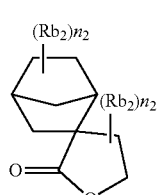
LC1-13 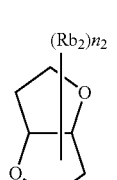
LC1-14 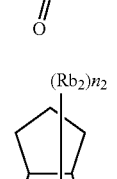
LC1-15 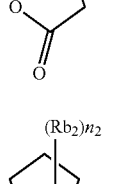
LC1-16 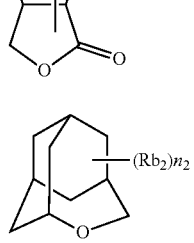

LC1-17 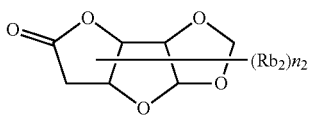

LC1-18 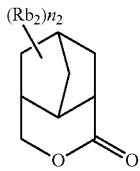

LC1-19 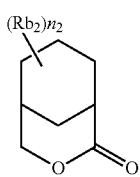

LC1-20 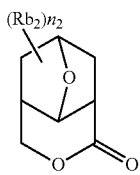

LC1-21 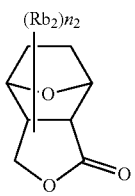

LC1-22 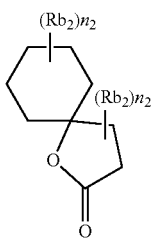

SL1-1 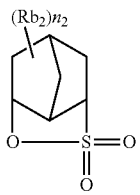

SL1-2 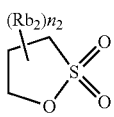

SL1-3 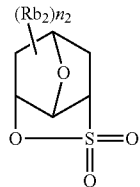

The lactone structure or sultone structure may or may not have a substituent ($Rb_2$). As the substituent ($Rb_2$), an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, or an acid-decomposable group is preferable, and an alkyl group having 1 to 4 carbon atoms, the cyano group, or the acid-decomposable group is more preferable. $n_2$ represents an integer of 0 to 4. In a case where $n_2$ is 2 or more, the substituents ($Rb_2$) which are present in a plural number may be the same as or different from each other. Further, the substituents ($Rb_2$) which are present in a plural number may be bonded to each other to form a ring.

As the repeating unit having a lactone structure or sultone structure, a repeating unit represented by General Formula (III) is preferable.

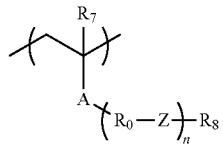
(III)

In General Formula (III),

A represents an ester bond (a group represented by —COO—) or an amide bond (a group represented by —CONH—).

n is the number of repetitions of the structure represented by —$R_0$—Z—, represents an integer of 0 to 5, and is preferably 0 or 1, and more preferably 0. In a case where n is 0, (—$R_0$—Z—)n is a single bond.

$R_0$ represents an alkylene group, a cycloalkylene group, or a combination thereof. In a case where $R_0$'s are present in a plural number, $R_0$'s which are present in a plural number may be the same as or different from each other.

The alkylene group or the cycloalkylene group of $R_0$ may have a substituent.

Z represents a single bond, an ether bond, an ester bond, an amide bond, a urethane bond, or a urea bond. In a case where Z's are present in a plural number, they may be the same as or different from each other.

Among those, Z is preferably an ether bond or an ester bond, more preferably an ester bond.

$R_8$ represents a monovalent organic group having a lactone structure or sultone structure.

Among those, any of the structures represented by General Formulae (LC1-1) to (LC1-22) and the structures represented by General Formulae (SL1-1) to (SL1-3) is preferably a group obtained by removing one hydrogen atom from one carbon atom constituting the lactone structure or sultone structure. In addition, it is preferable that the carbon atom from which one hydrogen atom is removed is not a carbon atom constituting the substituent ($Rb_2$).

$R_7$ represents a hydrogen atom, a halogen atom, or a monovalent organic group (preferably a methyl group).

As the repeating unit having a lactone structure or sultone structure, a repeating unit represented by General Formula (III-2) is also preferable.

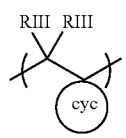

(III-2)

In General Formula (III-2), RIII's each independently represent a hydrogen atom or a substituent. Examples of the substituent include a halogen atom and a monovalent organic group (preferably a methyl group).

RIII is preferably a hydrogen atom.

cyc represents a group having a lactone structure or sultone structure.

Specifically, among those, any of the structures represented by General Formulae (LC1-1) to (LC1-22) and the structures represented by General Formulae (SL1-1) to (SL1-3) is preferably a group obtained by removing two hydrogen atoms from one carbon atom constituting the lactone structure or sultone structure. In addition, it is preferable that the carbon atom from which two hydrogen atoms are removed is not a carbon atom constituting the substituent ($Rb_2$).

The resin A may have a repeating unit having a carbonate structure. As the carbonate structure, a cyclic carbonate ester structure is preferable.

As the repeating unit having a cyclic carbonate ester structure, a repeating unit represented by General Formula (A-1) is preferable.

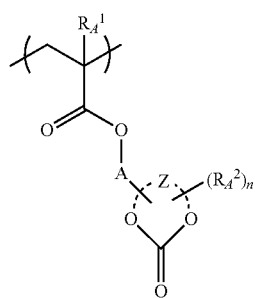

(A-1)

In General Formula (A-1), $R_A^1$ represents a hydrogen atom, a halogen atom, or a monovalent organic group (preferably a methyl group).

n represents an integer of 0 or more.

$R_A^2$ represents a substituent. In a case where n is 2 or more, $R_A^2$ which are present in a plural number may be the same as or different from each other.

A represents a single bond or a divalent linking group.

Z represents an atomic group that forms a monocycle or polycycle with a group represented by —O—CO—O— in the formula.

The resin A preferably includes the repeating unit described in paragraphs [0370] to [0414] of the specification of US2016/0070167A1 as a repeating unit having at least one selected from the group consisting of a lactone structure, a sultone structure, and a carbonate structure.

The resin A may have only one kind or two or more kinds of a repeating unit having at least one selected from the group consisting of a lactone structure, a sultone structure, and a carbonate structure.

Examples of a monomer corresponding to the repeating unit having at least one selected from the group consisting of a lactone structure, a sultone structure, and a carbonate structure are shown below.

In the following examples, the methyl group bonded to the vinyl group may be substituted with a hydrogen atom, a halogen atom, or a monovalent organic group.

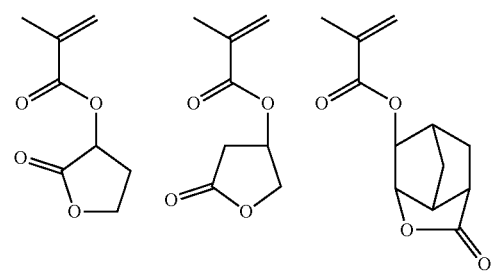

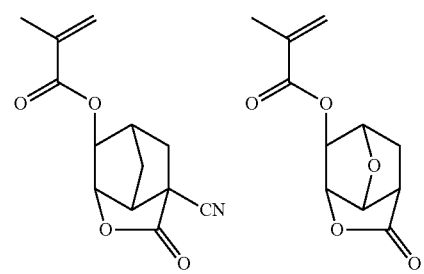

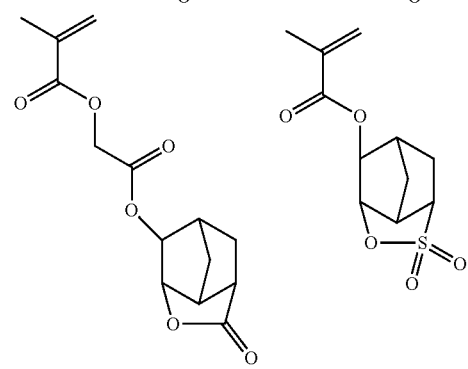

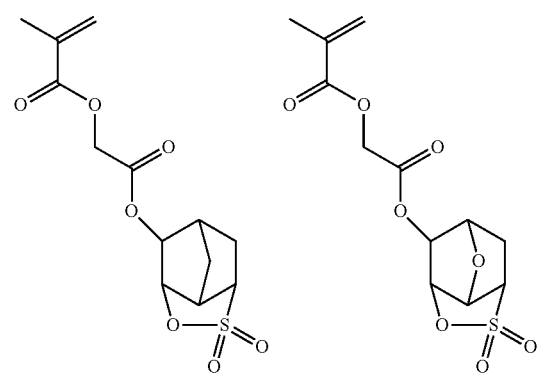

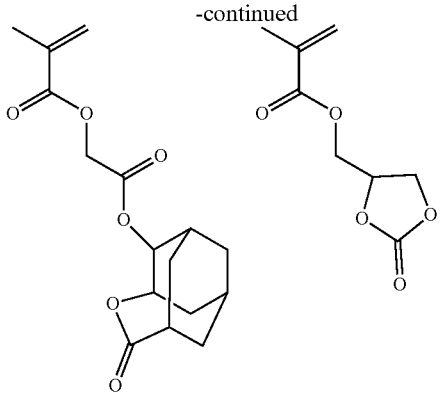
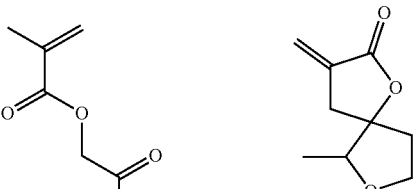
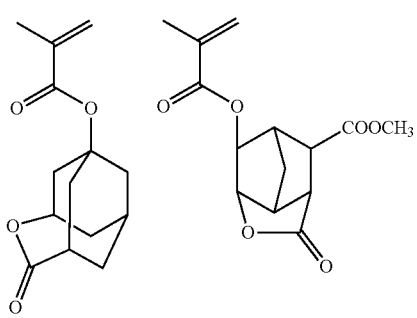
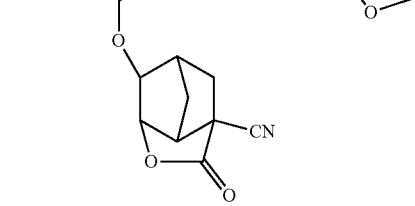
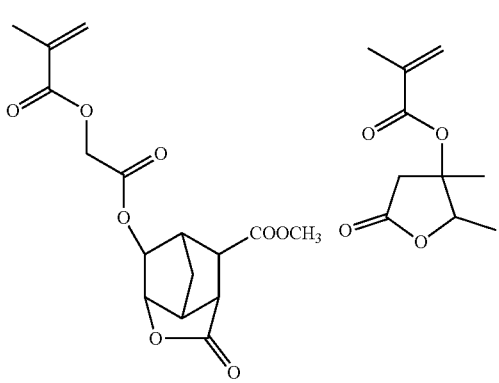
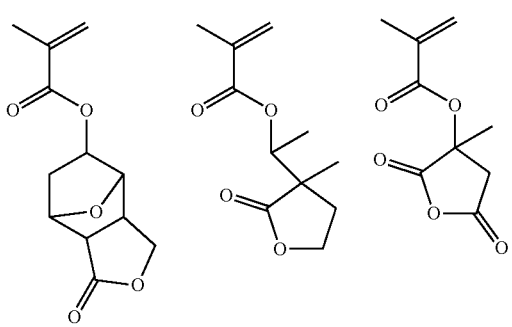

In a case where the resin A has a repeating unit having at least one selected from the group consisting of a lactone structure, a sultone structure, and a carbonate structure, a content of the repeating unit having at least one type selected from the group consisting of a lactone structure, a sultone structure, and a carbonate structure included in the resin A (in a case where the repeating units having at least one selected from the group consisting of a lactone structure, a sultone structure, and a carbonate structure are present in a plural number, a total content thereof) is preferably 5% to 70% by mole, more preferably 10% to 65% by mole, and still more preferably 20% to 60% by mole, with respect to all the repeating units in the resin A.

(Repeating Unit Having Acid-Decomposable Group)

The resin A may have a repeating unit having a polar group, in addition to the above-mentioned groups.

Examples of the polar group include a hydroxyl group, a cyano group, a carboxyl group, and a fluorinated alcohol group.

The repeating unit having a polar group is preferably a repeating unit having an alicyclic hydrocarbon structure substituted with a polar group. Further, the repeating unit having a polar group preferably does not have an acid-decomposable group. The alicyclic hydrocarbon structure in the alicyclic hydrocarbon structure substituted with a polar group is preferably an adamantyl group or a norbornane group.

Specific examples of a monomer corresponding to the repeating unit having a polar group are shown below, but the present invention is not limited to these specific examples.

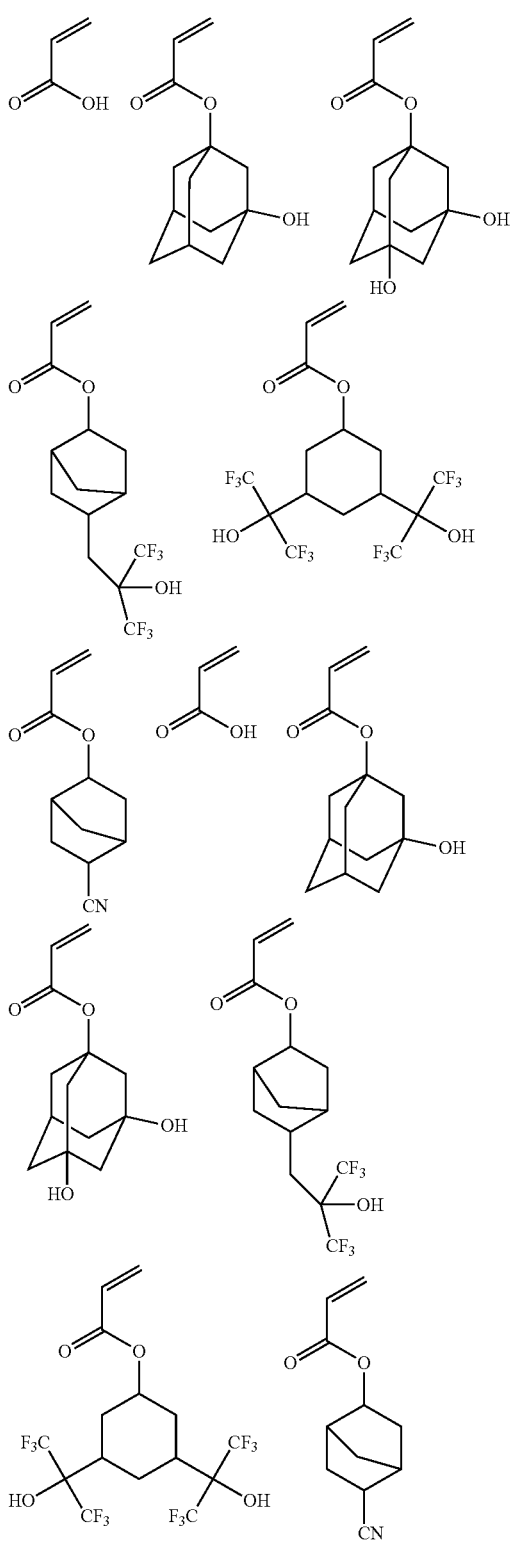

In addition to these, specific examples of the repeating unit having a polar group include the repeating units disclosed in paragraphs [0415] to [0433] of the specification of US2016/0070167A1.

The resin A may have only one kind or two or more kinds of the repeating units having a polar group.

In a case where the resin A has a repeating unit having a polar group, a content of the repeating unit having a polar group is preferably 5% to 40% by mole, more preferably 5% to 30% by mole, and still more preferably 10% to 25% by mole, with respect to all the repeating units in the resin A.

(Repeating Unit Having Neither Acid-Decomposable Group Nor Polar Group)

The resin A may further have a repeating unit having neither an acid-decomposable group nor a polar group, in addition to the above-mentioned groups. The repeating unit having neither an acid-decomposable group nor a polar group preferably has an alicyclic hydrocarbon structure. Examples of the repeating unit having neither an acid-decomposable group nor a polar group include the repeating units described in paragraphs [0236] and [0237] of the specification of US2016/0026083A1. Preferred examples of a monomer corresponding to the repeating unit having neither an acid-decomposable group nor a polar group are shown below.

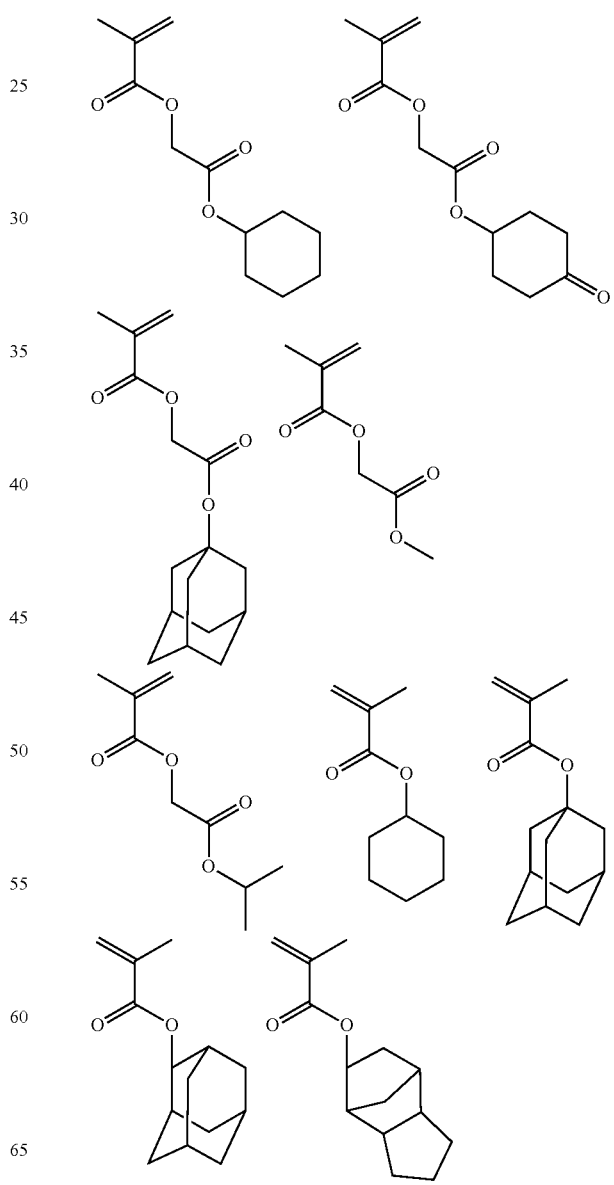

-continued

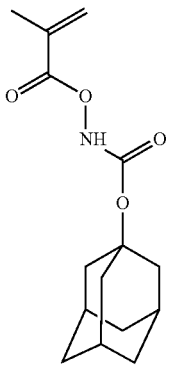

In addition to these, specific examples of the repeating unit having neither an acid-decomposable group nor a polar group include the repeating unit disclosed in paragraph [0433] of the specification of US2016/0070167A1.

The resin A may have only one kind or two or more kinds of the repeating units having neither an acid-decomposable group nor a polar group.

In a case where the resin A has the repeating unit having neither an acid-decomposable group nor a polar group, a content of the repeating unit having neither an acid-decomposable group nor a polar group is preferably 5% to 40% by mole, more preferably 5% to 30% by mole, and still more preferably 5% to 25% by mole, with respect to all the repeating units in the resin A.

In addition to the repeating structural units, the resin A may have a variety of repeating structural units, in addition to the above-mentioned repeating structural units, for the purpose of controlling dry etching resistance, suitability for a standard developer, adhesiveness to a substrate, and a resist profile, resolving power, heat resistance, sensitivity, and the like which are general characteristics required for a resist.

Examples of such a repeating structural unit include a repeating structural unit corresponding to a predetermined monomer, but are not limited thereto.

Examples of a predetermined monomer include a compound having one addition-polymerizable unsaturated bond, selected from acrylates, methacrylates, acrylamides, methacrylamides, allyl compounds, vinyl ethers, and vinyl esters.

In addition to these, an addition-polymerizable unsaturated compound that is copolymerizable with a monomer corresponding to the various repeating structural units may be used.

In the resin A, a content molar ratio of each repeating structural unit is appropriately set in order to adjust various performances.

In a case where the composition of the embodiment of the present invention is used for ArF exposure, it is preferable that the resin A has substantially no aromatic group from the viewpoint of transparency to ArF light. More specifically, the repeating unit having an aromatic group is preferably 5% by mole or less, more preferably 3% by mole or less, and ideally 0% by mole, with respect to all the repeating units in the resin A, that is, it is still more preferable that the repeating unit having an aromatic group is not included. In addition, the resin A preferably has a monocyclic or polycyclic alicyclic hydrocarbon structure.

In the resin A, all the repeating units may be constituted with (meth)acrylate-based repeating units. In this case, all of the repeating units may be methacrylate-based repeating units, all of the repeating units may be acrylate-based repeating units, and all of the repeating units are a combination of methacrylate-based repeating units and acrylate-based repeating units. Above all, a content of the acrylate-based repeating units is preferably 50% by mole or less with respect to all the repeating units of the resin A.

Besides, as the resin A, a known resin can be appropriately used. For example, the known resins disclosed in paragraphs [0055] to [0191] of the specification of US2016/0274458A1, paragraphs [0035] to [0085] of the specification of US2015/0004544A1, and paragraphs [0045] to [0090] of the specification of US2016/0147150A1 can be suitably used as the resin A.

In a case where the composition of the embodiment of the present invention is for KrF exposure, EB exposure, or EUV exposure, the resin A preferably has a repeating unit having an aromatic hydrocarbon group, and more preferably has a repeating unit including a phenolic hydroxyl group. Examples of the repeating unit including a phenolic hydroxyl group include a hydroxystyrene-based repeating unit and a hydroxystyrene (meth)acrylate-based repeating unit.

In a case where the composition of the embodiment of the present invention is for KrF exposure, EB exposure, or EUV exposure, it is preferable that the resin A has a structure in which a hydrogen atom of the phenolic hydroxyl group is protected with a group (leaving group) that leaves through decomposition by the action of an acid.

In this case, a content of the repeating unit having an aromatic hydrocarbon group included in the resin A is preferably 30% to 100% by mole, more preferably 40% to 100% by mole, and still more preferably 50% to 100% by mole, with respect to all the repeating units in the resin A.

The weight-average molecular weight of the resin A is preferably 1,000 to 200,000, more preferably 2,000 to 20,000, still more preferably 3,000 to 15,000, and particularly preferably 3,000 to 12,000. The dispersity (Mw/Mn) is usually 1.0 to 3.0, preferably 1.0 to 2.6, more preferably 1.0 to 2.0, and still more preferably 1.1 to 2.0.

The resin A may be used singly or in combination of two or more kinds thereof.

The content of the resin A in the composition is generally 20% by mass or more in many cases, and is preferably 40% by mass or more, more preferably 60% by mass or more, and still more preferably 75% by mass or more, with respect to the total solid content in the composition. The upper limit is not particularly limited, but is preferably 95% by mass or less, and more preferably 90% by mass or less.

In addition, the solid content is intended to mean the components excluding the solvent in the composition.

<Specific Photoacid Generator>

The composition of the embodiment of the present invention includes a specific photoacid generator.

The specific photoacid generator is a compound represented by General Formula (b1) which will be described later.

The specific acid generator is a compound that generates an acid upon irradiation with actinic rays or radiation.

An acid generated from the specific photoacid generator upon irradiation with actinic rays or radiation has a pka of 1.0 or less, preferably 0.5 or less, and more preferably 0.0 or less.

The molecular weight of the specific photoacid generator is preferably 3,000 or less, more preferably 2,000 or less, and still more preferably 1,000 or less. The lower limit is not particularly limited, but is usually 100 or more.

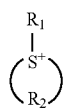

(b1)

In General Formula (31), the substituent represented by $R_1$ has an anionic group or the group represented by $R_2$ has an anionic group. That is, in a case where the substituent represented by $R_1$ has an anionic group, $R_2$ has no anionic group, and in a case where $R_2$ has an anionic group, the substituent represented by $R_1$ has no anionic group. In other words, in a case where the substituent represented by $R_1$ has no anionic group, $R_2$ has an anionic group, and in a case where $R_2$ has no anionic group, the substituent represented by $R_1$ has an anionic group.

Furthermore, even in a case where $R_2$ has an anionic group, $R_2$ is a group forming a heterocycle having at least one or more heteroatoms other than $S^+$, which may have a substituent, together with S.

The anionic group may be a monovalent group or a divalent or higher valent group. Among those, the anionic group is preferably the monovalent group.

The number of anionic groups contained in one molecule of the specific photoacid generator is preferably 1.

Preferred aspects of the anionic group will be described later.

In General Formula (b1), $R_1$ represents a substituent.

The substituent is preferably an organic group. The organic group generally has 1 to 30 carbon atoms, and preferably has 1 to 20 carbon atoms. Examples of the organic group include an aryl group (preferably a phenyl group or a naphthyl group) which may further have a substituent, and an alkyl group which may further have a substituent (preferably having 1 to 5 carbon atoms).

Furthermore, a form in which the substituent represented by $R_1$ has an anionic group is not particularly limited, and the substituent represented by $R_1$ itself may be an anionic group or the anionic group may be included as a part of the substituents represented by $R_1$.

In General Formula (b1), $R_2$ represents a group forming a heterocycle having at least one heteroatom other than $S^+$, which may have a substituent, together with $S^+$ in General Formula (b1).

As the heteroatom other than $S^+$, an oxygen atom, a nitrogen atom, or a sulfur atom is preferable.

Further, the heterocycle may be fused with another ring. That is, the heterocycle may be either a monocycle or a polycycle.

The heterocycle is preferably a 5- to 7-membered ring, and more preferably a 6-membered ring.

Examples of the substituent which may be contained in the heterocycle include an anionic group.

The structure of $R_2$ is not particularly limited as long as it has one or more heteroatoms (atoms other than a carbon atom, for example, one or more selected from the group consisting of an oxygen atom, a nitrogen atom, and a sulfur atom) as an atom which contributes to ring formation.

Examples of $R_2$ include a group formed by the combination of one or more groups selected from the group consisting of an ether group (—O—), an ester group (—COO—), a thioether group (—S—), —SO$_2$—, and —NR— (R represents a hydrogen atom or a substituent (for example, an anionic group)), and one or more groups selected from the group consisting of a divalent hydrocarbon group (for example, an alkylene group, an alkenylene group (example: —CH=CH—), an alkynylene group (example: —C≡C—), and an arylene group) which may have a substituent (for example, an anionic group) and a carbonyl group.

$R_2$ preferably has 2 or more carbon atoms, more preferably has 2 to 20 carbon atoms, still more preferably has 2 to 15 carbon atoms, and particularly preferably has 4 to 13 carbon atoms.

In a case where $R_2$ has an anionic group, the form in which $R_2$ has the anionic group is not particularly limited, and for example, a form in which $R_2$ has a substituent and this substituent is an anionic group is preferable. This form has the same meaning as the form in which the substituent which may be contained in the heterocycle is an anionic group.

In a case where $R_2$ has anionic groups, the total number of anionic groups contained in $R_2$ is preferably 1.

Among those, $R_2$ is preferably a group represented by General Formula (b1-$R_2$).

*-Rp$_1$-Rq-Rp$_2$-* (b1-R$_2$)

In General Formula (b1-$R_2$), $Rp_1$ and $Rp_2$ each independently represent a divalent hydrocarbon group which may have a substituent (preferably having 1 to 15 carbon atoms).

The divalent hydrocarbon group is preferably an alkylene group, an alkenylene group, an alkynylene group, or an arylene group, and more preferably the alkylene group or the arylene group.

The alkylene group preferably has 1 to 5 carbon atoms, more preferably has 1 or 2 carbon atoms, and still more preferably has 2 carbon atoms.

The alkenylene group and the alkynylene group each preferably have 2 to 5 carbon atoms, more preferably 1 or 2 carbon atoms, and still more preferably 2 carbon atoms.

The arylene group preferably has 6 to 12 carbon atoms, and more preferably 6 carbon atoms. Further, in $Rp_1$ or $Rp_2$ in a case where it is an arylene group, it is preferable that an atom bonded to * and an atom bonded to Rq in the arylene group are disposed adjacent to each other.

In addition, the alkylene group, the alkenylene group, the alkynylene group, and the arylene group may have a substituent, and the substituent may be an anionic group.

$Rp_1$ and $Rp_2$ may be the same as or different from each other. Among those, it is preferable that $Rp_1$ and $Rp_2$ are the same as each other.

Rq represents an ether group (—O—), an ester group, a thioether group, —SO$_2$—, or —NR— (R is a hydrogen atom or a substituent (for example, an anionic group or an alkyl group)).

Among those, Rq is preferably an ether group or —NR—. Further, in a case where Rq is —NR—, it is preferable that R is an anionic group.

* represents a bonding position to $S^k$ in General Formula (b1).

More specifically, the group represented by General Formula (b1-$R_2$) is preferably *-alkylene group-O-alkylene group-*, *-arylene group-O-arylene group-*, or *-alkylene group-NR-alkylene group-*. R in this case is preferably an anionic group.

In addition, in a case where an aromatic ring group is disposed at a position bonded to S⁺ in $R_1$, at least one of $Rp_1$ or $Rp_2$ represents a group other than the aromatic ring group (for example, an arylene group).

In General Formula (b1), an aromatic ring group is not disposed at at least one of a position bonded to S⁺ in $R_1$ and two positions bonded to S⁺ in $R_2$. In other words, an aromatic ring group is not disposed at at least one of the position bonded to S⁺ in $R_1$ and the two positions bonded to S⁺ in $R_2$.

That is, the specific photoacid generator does not include a compound in the form in which S⁺ is directly bonded to the three aromatic ring groups.

The anionic group is a group having anionicity, and examples thereof include a group having a carboxylate anion group (—COO⁻ or —CH₂COO⁻), a group having a sulfonate anion group (—SO₃⁻), a group having an amide anion group (—N⁻—), a group having a carbanion group (>C⁻—), a group having a phosphate anion group (—OP(=O)(OH)O⁻ and —OP(=O)(O⁻)₂, a group having a sulfate anion group (—OS(=O)₂O⁻), a group having a phosphonate anion group (—P(=O)(OH)O⁻ and —P(=O)(O⁻)₂), and a group having a phosphinate anion group (—PH(=O)O⁻). Furthermore, the group having each of these anion groups may be each anion group itself or may be a group including each anion group in a part thereof. Among those, the anionic group is preferably a group represented by any of General Formulae (b1-1) to (b1-3).

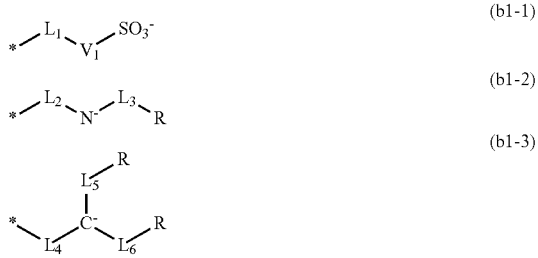

In General Formula (b1-1), $L_1$ represents a single bond or a divalent linking group.

Examples of the divalent linking group include an ether group, a carbonyl group, an ester group, a thioether group, —SO₂—, —NR— (R is a hydrogen atom or an alkyl group), a divalent hydrocarbon group (for example, an alkylene group, an alkenylene group (example: —CH=CH—), an alkynylene group (example: —C≡C—), and an arylene group), and a group formed by combination of these groups.

Examples of the combined group include -ether group-arylene group (preferably a phenylene group)-ester group-, —NR (preferably —NH—)-carbonyl group-, —NR (preferably —NH—)—SO₂—, and -alkylene group (preferably having 1 to 3 carbon atoms)-ester group-.

In General Formula (b1-1), $V_1$ represents a single bond or a hydrocarbon group which may have a fluorine atom.

As the hydrocarbon group, an alkylene group, an alkenylene group, an alkynylene group, or an arylene group is preferable, and the alkylene group is more preferable.

The alkylene group, the alkenylene group, and the alkynylene group may be linear or branched, or may have a cyclic structure. Further, the alkylene group preferably has 1 to 5 carbon atoms, and the alkenylene group and the alkynylene group each preferably have 2 to 5 carbon atoms.

The arylene group preferably has 6 to 15 carbon atoms.

The hydrocarbon group (the alkylene group, the alkenylene group, the alkynylene group, the arylene group, and the like) may have a fluorine atom, and for example, the alkylene group may be a fluoroalkylene group (including a perfluoroalkylene group).

* represents a bonding position.

In General Formula (b1-2), $L_2$ and $L_3$ each independently represent a single bond or a divalent linking group.

Examples of the divalent linking group include an ether group, a carbonyl group, an ester group, a thioether group, —SO₂—, —NR— (R is a hydrogen atom or an alkyl group), a divalent hydrocarbon group (for example, an alkylene group, an alkenylene group (example: —CH=CH—), an alkynylene group (example: —C≡C—), and an arylene group), and a group formed by combination of these groups.

Examples of the combined group include an -ether group-SO₂—.

Among those, the divalent linking group is preferably a group having —SO₂— (which may be —SO₂— itself or a group including —SO₂— in a part thereof).

Among those, in $L_2$ and $L_3$, it is preferable that at least one of the groups directly bonded to N⁻ is —SO₂⁻, and it is more preferable that both of the groups are —SO₂⁻.

In General Formula (b1-2),

R represents an organic group.

Examples of the organic group include a hydrocarbon group which may have a substituent.

Examples of the hydrocarbon group include an alkyl group, an alkenyl group, an alkynyl group, and an aryl group.

The alkyl group, the alkenyl group, and the alkynyl group may be linear or branched. The alkyl group preferably has 1 to 5 carbon atoms, and the alkenyl group and the alkynyl group each preferably have 2 to 5 carbon atoms.

The aryl group preferably has 6 to 15 carbon atoms.

The hydrocarbon group (the alkyl group, the alkenyl group, the alkynyl group, the aryl group, and the like) preferably has a fluorine atom as a substituent, and for example, the alkyl group may be a fluoroalkyl group (including a perfluoroalkyl group such as a perfluoromethyl group).

* represents a bonding position.

In addition, in a case where the anionic group is a group represented by General Formula (b1-2), it is preferable that $R_2$ in General Formula (b1) has an anionic group.

In General Formula (b1-3), $L_4$, $L_5$, and $L_6$ each independently represent a single bond or a divalent linking group.

Examples of the divalent linking group include an ether group, a carbonyl group, an ester group, a thioether group, —SO₂—, —NR— (R is a hydrogen atom or an alkyl group), a divalent hydrocarbon group (for example, an alkylene group, an alkenylene group (example: —CH=CH—), an alkynylene group (example: —C≡C—), and an arylene group) which may have a substituent, and a group formed by combination of these groups.

The divalent hydrocarbon group is preferably an alkylene group (preferably having 1 to 3 carbon atoms). Further, as the substituent which may be contained in the divalent hydrocarbon group, a fluorine atom is preferable, and for example, the alkylene group may be a fluoroalkylene group (including a perfluoroalkylene group such as a perfluoromethylene group).

Among those, examples of $L_4$ include -ester group-perfluoroalkylene group (preferably having 1 to 3 carbon atoms) —$SO_2^-$. Further, in $L_4$, the group directly bonded to $C^-$ is preferably —$SO_2$—.

In General Formula (b1-3),

R's each independently represent an organic group.

Examples of the organic group include the same group as the organic group represented by R in General Formula (b1-2).

* represents a bonding position.

Among those, the anionic group is more preferably the group represented by General Formula (b1-1) or the group represented by General Formula (b1-3), and more preferably the group represented by General Formula (b1-1).

The specific photoacid generator is preferably a compound represented by General Formula (ZI-3) or a compound represented by General Formula (ZI-4).

(Compound Represented by General Formula (ZI-3))

The compound represented by General Formula (ZI-3) is a compound having a phenacylsulfonium structure.

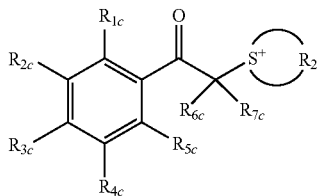

(ZI-3)

In General Formula (ZI-3), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, an arylthio group, or an anionic group.

$R_{6c}$ and $R_{7c}$ each independently represent a hydrogen atom, an alkyl group, a cycloalkyl group, a halogen atom, a cyano group, an aryl group, or an anionic group.

Any two or more of $R_{1c}$, ..., or $R_{5c}$, $R_{5c}$ and $R_{6c}$, and $R_{6c}$ and $R_{7c}$ may be bonded to each other to form a ring, and the ring's may each independently include an oxygen atom, a sulfur atom, a carbonyl group, an ester group, and/or an amido group.

Examples of the ring include an aromatic or non-aromatic hydrocarbon ring, an aromatic or non-aromatic heterocycle, and a polycycle formed by combination of two or more of these rings. Examples of the ring include a 3- to 10-membered ring, a 4- to 8-membered ring is preferable, and a 5- or 6-membered ring is more preferable. It should be noted that it is preferable that the ring formed by the bonding of $R_{5c}$ and $R_{6c}$ and the ring formed by the bonding of $R_{6c}$ and $R_{7c}$ do not have aromaticity.

Examples of the group formed by the combination of any two or more of $R_{1c}$ to $R_{5c}$, and $R_{6c}$ and $R_{7c}$ include a butylene group and a pentylene group.

The group formed by the combination of $R_{5c}$ and $R_{6c}$ is preferably a single bond or an alkylene group. Examples of the alkylene group include a methylene group and an ethylene group.

In General Formula (ZI-3), $R_2$ represents a group forming a heterocycle having at least one heteroatom other than $S^+$, which may have a substituent, together with $S^+$.

$R_2$ in General Formula (ZI-3) has the same meaning as $R_2$ in General Formula (b1), and a preferred range is also the same.

In General Formula (ZI-3), any one of $R_{1c}$, ..., or $R_{7c}$ is an anionic group, or $R_2$ is a group having an anionic group.

In General Formula (ZI-3), it is preferable that only one anionic group is present. Furthermore, even in a case where $R_2$ is a group having an anionic group, $R_2$ is a group forming a heterocycle having at least one heteroatom other than $S^+$, which may have a substituent, together with $S^+$.

In a case where any one of $R_{1c}$, ..., or $R_{7c}$ is an anionic group, it is preferable that one of $R_{1c}$ to $R_{7c}$ is an anionic group represented by any of General Formulae (b1-1) to (b1-3).

In addition, in a case where $R_2$ is a group having an anionic group, it is preferable that $R_2$ is a group represented by General Formula (b1-$R_2$), Rq is —NR—, and R is an anionic group represented by any one of General Formula (b1-1) to (b1-3).

Among those, $R_{3c}$ is preferably the anionic group itself represented by any of General Formulae (b1-1) to (b1-3).

(Compound Represented by General Formula (ZI-4))

Next, the compound represented by Formula (ZI-4) will be described.

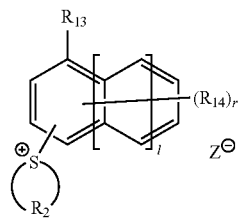

(ZI-4)

In General Formula (ZI-4), l represents an integer of 0 to 2.

r represents an integer of 0 to 8.

$R_{13}$ represents a hydrogen atom, a fluorine atom, a hydroxyl group, an alkyl group, an alkoxy group, an alkoxycarbonyl group, a group having a cycloalkyl group (which may be the cycloalkyl group itself or a group including the cycloalkyl group in a part thereof), or an anionic group. These groups may have a substituent where available.

$R_{14}$ represents a hydroxyl group, an alkyl group, an alkoxy group, an alkoxycarbonyl group, an alkylcarbonyl group, an alkylsulfonyl group, a cycloalkylsulfonyl group, a group having a cycloalkyl group (which may be the cycloalkyl group itself or a group including the cycloalkyl group in a part thereof), or an anionic group. These groups may have a substituent where available. In a case where $R_{14}$'s are present in a plural number, they each independently represent the group such as a hydroxyl group.

The alkyl group in each of $R_{13}$ and $R_{14}$ is linear or branched, preferably has 1 to 10 carbon atoms, and is more preferably a methyl group, an ethyl group, an n-butyl group, a t-butyl group, or the like.

$R_2$ represents a group forming a heterocycle having at least one heteroatom other than $S^+$, which may have a substituent, together with $S^+$.

$R_2$ in General Formula (ZI-4) has the same meaning as $R_2$ in General Formula (b1), and a preferred range is also the same.

It should be noted that an aromatic ring group is not disposed at at least one of the two positions bonded to S⁺ in $R_2$. For example, in a case where $R_2$ is a group represented by General Formula (b1-R2), $p_1$ or $Rp_2$ is a group other than an aromatic ring group (for example, an arylene group).

In General Formula (ZI-4), $R_{13}$ and any one of $R_{14}$'s which may be present in a plural number are each an anionic group, or $R_2$ is a group having an anionic group.

In General Formula (ZI-4), it is preferable that only one anionic group is present. Furthermore, even in a case where $R_2$ is a group having an anionic group, $R_2$ is a group forming a heterocycle having at least one heteroatom other than S⁺, which may have a substituent, together with S.

In a case where $R_{13}$ and any one of $R_{14}$'s which may be present in a plural number are each an anionic group, it is preferable that $R_{13}$ and any one of $R_{14}$'s which may be present in a plural number are each an anionic group represented by any of General Formulae (b1-1) to (b1-3).

In addition, in a case where $R_2$ is a group having an anionic group, it is preferable that $R_2$ is a group represented by General Formula (b1-R$_2$), Rq is —NR—, and R is an anionic group represented by any one of General Formula (b1-1) to (b1-3).

The specific photoacid generators may be used singly or in combination of two or more kinds thereof.

A content of the specific photoacid generator (in a case where the photoacid generators are present in a plurality of kinds, a total content thereof) in the composition is preferably 0.1% to 35% by mass, more preferably 0.5% to 25% by mass, still more preferably 3% to 20% by mass, and particularly preferably 5% to 13% by mass, with respect to a total solid content of the composition.

<Another Photoacid Generator>

The composition of the embodiment of the present invention may include a photoacid generator other than the specific photoacid generator. Hereinafter, the photoacid generator other than the specific photoacid generator is also referred to as another photoacid generator.

Such another photoacid generator is a compound that generates an acid upon irradiation with actinic rays or radiation, and is also a compound other than the specific photoacid generator.

As such another photoacid generator, a compound that generates an organic acid upon irradiation with actinic rays or radiation is preferable. Examples thereof include a sulfonium salt compound, an iodonium salt compound, a diazonium salt compound, a phosphonium salt compound, an imidosulfonate compound, an oxime sulfonate compound, a diazodisulfone compound, a disulfone compound, and an o-nitrobenzyl sulfonate compound.

Such another photoacid generator may be a zwitterion, but cannot be the specific photoacid generator.

As such another photoacid generators, known compounds that generate an acid upon irradiation with actinic rays or radiation can be used singly or as a mixture thereof, appropriately selected and used. For example, the known compounds disclosed in paragraphs [0125] to [0319] of the specification of US2016/0070167A1, paragraphs [0086] to [0094] of the specification of US2015/0004544A1, and paragraphs [0323] to [0402] of the specification of US2016/0237190A1 can be suitably used as such another photoacid generator.

As such another photoacid generator, for example, a compound represented by General Formula (Z1), a compound represented by General Formula (ZII), or a compound represented by General Formula (ZIII) is preferable.

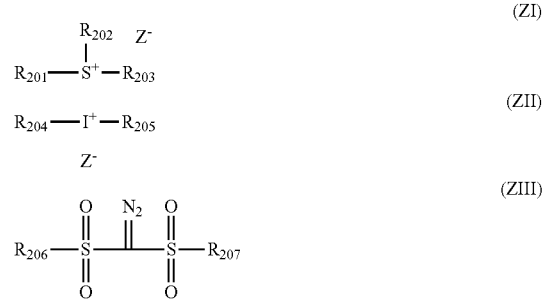

In General Formula (Z1), $R_{201}$, $R_{202}$, and $R_{203}$ each independently represent an organic group.

The organic group as each of $R_{201}$, $R_{202}$, and $R_{203}$ generally has 1 to 30 carbon atoms, and preferably has 1 to 20 carbon atoms. In addition, two of $R_{201}$ to $R_{203}$ may be bonded to each other to form a ring structure, and the ring may include an oxygen atom, a sulfur atom, an ester group, an amido group, or a carbonyl group. Examples of the group formed by the bonding of two of $R_{201}$ to $R_{203}$ include an alkylene group (for example, a butylene group and a pentylene group), and —CH$_2$—CH$_2$—O—CH$_2$—CH$_2$—. Z⁻ represents an anion.

Suitable aspects of the cation in General Formula (ZI) include the corresponding groups in a compound (ZI-1), a compound (ZI-2), a compound (ZI-3b), and a compound (ZI-4b) which will be described later.

Furthermore, such another photoacid generator may be a compound having a plurality of structures represented by General Formula (ZI). For example, at least one of $R_{201}, \ldots,$ or $R_{203}$ of the compound represented by General Formula (ZI) and at least one of $R_{201}, \ldots,$ or $R_{203}$ of another compound represented by General Formula (ZI) are bonded via a single bond or a linking group.

First, the compound (ZI-1) will be described.

The compound (ZI-1) is an arylsulfonium compound in which at least one of $R_{201}, \ldots,$ or $R_{203}$ in General Formula (ZI) is an aryl group, that is, a compound having arylsulfonium as a cation.

In the arylsulfonium compound, any of $R_{201}$ to $R_{203}$ may be an aryl group, or some of $R_{201}$ to $R_{203}$ may be an aryl group, and the rest may be an alkyl group or a cycloalkyl group.

Examples of the arylsulfonium compound include a triarylsulfonium compound, a diarylalkylsulfonium compound, an aryldialkylsulfonium compound, a diarylcycloalkylsulfonium compound, and an aryldicycloalkylsulfonium compound.

As the aryl group included in the arylsulfonium compound, a phenyl group or a naphthyl group is preferable, and the phenyl group is more preferable. The aryl group may be an aryl group which has a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium compound has two or more aryl groups, the two or more aryl groups may be the same as or different from each other.

The alkyl group or the cycloalkyl group contained in the arylsulfonium compound, as necessary, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

The aryl group, the alkyl group, and the cycloalkyl group of each of $R_{201}$ to $R_{203}$ may each independently have an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a halogen atom, a hydroxyl group, or a phenylthio group as a substituent.

Next, the compound (ZI-2) will be described.

The compound (ZI-2) is a compound in which $R_{201}$ to $R_{203}$ in Formula (ZI) each independently represent an organic group having no aromatic ring. Here, the aromatic ring also includes an aromatic ring including a heteroatom.

The organic group having no aromatic ring as each of $R_{201}$ to $R_{203}$ generally has 1 to 30 carbon atoms, and preferably 1 to 20 carbon atoms.

$R_{201}$ to $R_{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Preferred examples of the alkyl group and the cycloalkyl group of each of $R_{201}$ to $R_{203}$ include a linear alkyl group having 1 to 10 carbon atoms or branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group).

$R_{201}$ to $R_{203}$ may be further substituted with a halogen atom, an alkoxy group (for example, having 1 to 5 carbon atoms), a hydroxyl group, a cyano group, or a nitro group.

Next, the compound (ZI-3b) will be described.

The compound (ZI-3b) is a compound represented by General Formula (ZI-3b) and having a phenacylsulfonium salt structure.

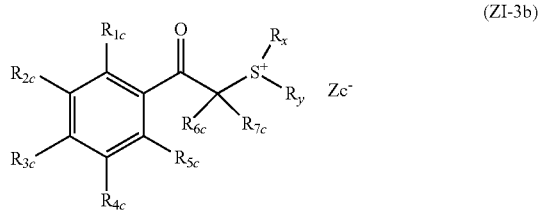

(ZI-3b)

In General Formula (ZI-3b), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ each independently represent a hydrogen atom, an alkyl group, a cycloalkyl group, a halogen atom, a cyano group, or an aryl group.

$R_x$ and $R_y$ each independently represent an alkyl group, a cycloalkyl group, a 2-oxoalkyl group, a 2-oxocycloalkyl group, an alkoxycarbonylalkyl group, an allyl group, or a vinyl group.

Any two or more of $R_{1c}, \ldots,$ or $R_{5c}$, $R_{5c}$ and $R_{6c}$, $R_{6c}$ and $R_{7c}$, $R_{5c}$ and $R_x$, or $R_x$ and $R_y$ may be bonded to each other to form a ring, and the ring may each independently include an oxygen atom, a sulfur atom, a ketone group, an ester bond, or an amide bond.

Examples of the ring include an aromatic or non-aromatic hydrocarbon ring, an aromatic or non-aromatic heterocycle, and a polycyclic fused ring in which two or more of these rings are combined. Examples of the ring include a 3- to 10-membered ring, and the ring is preferably a 4- to 8-membered ring, and more preferably a 5- or 6-membered ring.

Examples of the group formed by the combination of any two or more of $R_{1c}, \ldots,$ or $R_{5c}$, $R_{6c}$ and $R_{7c}$, and $R_x$ and $R_y$, include a butylene group and a pentylene group.

As the group formed by the combination of $R_{5c}$ and $R_{6c}$, and $R_{5c}$ and $R_x$, a single bond or an alkylene group is preferable. Examples of the alkylene group include a methylene group and an ethylene group.

$Zc^-$ represents an anion.

Next, the compound (ZI-4b) will be described.

The compound (ZI-4b) is a compound represented by General Formula (ZI-4b).

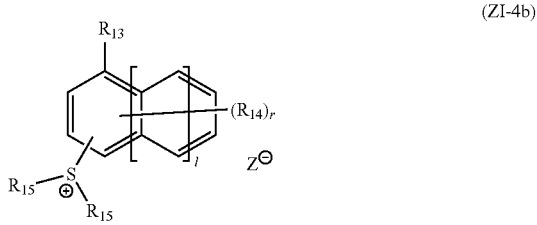

(ZI-4b)

In General Formula (ZI-4b), l represents an integer of 0 to 2.

r represents an integer of 0 to 8.

$R_{13}$ represents a hydrogen atom, a fluorine atom, a hydroxyl group, an alkyl group, an alkoxy group, an alkoxycarbonyl group, or a group having a cycloalkyl group (which may be the cycloalkyl group itself or a group including the cycloalkyl group in a part thereof). Such a group may have a substituent.

$R_{14}$ represents a hydroxyl group, an alkyl group, an alkoxy group, an alkoxycarbonyl group, an alkylcarbonyl group, an alkylsulfonyl group, a cycloalkylsulfonyl group, or a group having a cycloalkyl group (which may be the cycloalkyl group itself or a group including the cycloalkyl group in a part thereof). Such a group may have a substituent. In a case where $R_{14}$'s are present in a plural number, they each independently represent the group such as a hydroxyl group.

$R_{15}$'s each independently represent an alkyl group, a cycloalkyl group, or a naphthyl group. Such a group may have a substituent. Two of $R_{15}$'s may be bonded to each other to form a ring. In a case where two of $R_{15}$'s are bonded to each other to form a ring, the ring skeleton may include a heteroatom such as an oxygen atom and a nitrogen atom. In one aspect, it is preferable that two of $R_{15}$'s are alkylene groups and are bonded to each other to form a ring structure.

$Z^-$ represents an anion.

In General Formula (ZI-4b), the alkyl groups of each of $R_{13}$, $R_{14}$, and $R_{15}$ are linear or branched. The alkyl group preferably has 1 to 10 carbon atoms. As the alkyl group, a methyl group, an ethyl group, an n-butyl group, a t-butyl group, or the like is preferable.

Next, General Formula (ZII) and General Formula (ZIII) will be described.

In General Formula (ZII) and General Formula (ZIII), $R_{204}$ to $R_{207}$ each independently represent an aryl group, an alkyl group, or a cycloalkyl group.

The aryl group of each of $R_{204}$ to $R_{207}$ is preferably a phenyl group or a naphthyl group, and more preferably the phenyl group. The aryl group of each of $R_{204}$ to $R_{207}$ may be an aryl group which has a heterocycle having an oxygen atom, a nitrogen atom, a sulfur atom, or the like. Examples of the skeleton of the aryl group having a heterocycle include pyrrole, furan, thiophene, indole, benzofuran, and benzothiophene.

As the alkyl group and the cycloalkyl group of each of $R_{204}$ to $R_{207}$, a linear alkyl group having 1 to 10 carbon atoms or branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group) is preferable.

The aryl group, the alkyl group, and the cycloalkyl group of each of $R_{204}$ to $R_{207}$ may each independently have a substituent. Examples of the substituent that the aryl group, alkyl group and cycloalkyl group of each of $R_{204}$ to $R_{207}$ may have include, for example, an alkyl group (for example, having 1 to 15 carbon atoms) and a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, and a phenylthio group.

$Z^-$ represents an anion.

As $Z^-$ in General Formula (ZI), $Z^-$ in General Formula (ZII), $Zc^-$ in General Formula (ZI-3b), and $Z^-$ in General Formula (ZI-4b), an anion represented by General Formula (3) is preferable.

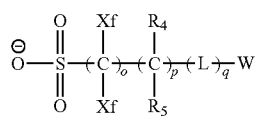

(3)

In General Formula (3), o represents an integer of 1 to 3. p represents an integer of 0 to 10. q represents an integer of 0 to 10.

Xf represents a fluorine atom or an alkyl group substituted with at least one fluorine atom. The alkyl group preferably has 1 to 10 carbon atoms, and more preferably has 1 to 4 carbon atoms. In addition, a perfluoroalkyl group is preferable as the alkyl group substituted with at least one fluorine atom.

Xf is preferably a fluorine atom or a perfluoroalkyl group having 1 to 4 carbon atoms, and more preferably a fluorine atom or $CF_3$. Above all, it is more preferable that both Xf s are fluorine atoms.

$R_4$ and $R_5$ each independently represent a hydrogen atom, a fluorine atom, an alkyl group, or an alkyl group substituted with at least one fluorine atom. In a case where $R_4$'s and $R_5$'s are each present in a plural number, $R_4$'s which are present in a plural number and $R_5$'s which are present in a plural number may be the same as or different from each other.

The alkyl group represented by each of $R_4$ and $R_5$ may have a substituent, and preferably has 1 to 4 carbon atoms. $R_4$ and $R_5$ are each preferably a hydrogen atom.

Specific examples and suitable aspects of the alkyl group substituted with at least one fluorine atom are the same as the specific examples and suitable aspects, respectively, of Xf in General Formula (3).

L represents a divalent linking group. In a case where L's are present in a plural number, L's may be the same as or different from each other.

Examples of the divalent linking group include —COO—, —OCO—, —CONH—, —NHCO—, —CO—, —O—, —S—, —SO—, —SO₂—, an alkylene group (preferably having 1 to 6 carbon atoms), a cycloalkylene group (preferably having 3 to 15 carbon atoms), an alkenylene group (preferably having 2 to 6 carbon atoms), and a divalent linking group formed by combination of a plurality of these groups. Among those, —COO—, —OCO—, —CONH—, —NHCO—, —CO—, —O—, —SO₂—, —COO-alkylene group-, —OCO-alkylene group-, —CONH-alkylene group-, or —NHCO-alkylene group- is preferable, and —COO—, —OCO—, —CONH—, —SO₂—, —COO-alkylene group -, or —OCO-alkylene group- is more preferable.

W represents an organic group including a cyclic structure. Among these, W is preferably a cyclic organic group.

Examples of the cyclic organic group include an alicyclic group, an aryl group, and a heterocyclic group.

The alicyclic group may be either a monocycle or a polycycle. Examples of the monocyclic alicyclic group include monocyclic cycloalkyl groups such as a cyclopentyl group, a cyclohexyl group, and a cyclooctyl group. Examples of the polycyclic alicyclic group include polycyclic cycloalkyl groups such as a norbornyl group, a tricyclodecanyl group, a tetracyclodecanyl group, a tetracyclododecanyl group, and an adamantyl group. Among those, an alicyclic group having a bulky structure having 7 or more carbon atoms is preferable, and examples thereof include a norbornyl group, a tricyclodecanyl group, a tetracyclodecanyl group, a tetracyclododecanyl group, and an adamantyl group.

The aryl group may be either a monocycle or a polycycle. Examples of the aryl group include a phenyl group, a naphthyl group, a phenanthryl group, and an anthryl group.

The heterocyclic group may be either a monocycle or a polycycle. The polycycle can further suppress acid diffusion. Further, the heterocyclic group may have aromaticity or may not have aromaticity. Examples of the aromatic heterocycle include a furan ring, a thiophene ring, a benzofuran ring, a benzothiophene ring, a dibenzofuran ring, a dibenzothiophene ring, and a pyridine ring. Examples of the heterocycle not having aromaticity include a tetrahydropyran ring, a lactone ring, a sultone ring, and a decahydroisoquinoline ring. Examples of the lactone ring and the sultone ring include the lactone structure and the sultone structure exemplified in the aforementioned resin. As the heterocycle in the heterocyclic group, the furan ring, the thiophene ring, the pyridine ring, or the decahydroisoquinoline ring is preferable.

The cyclic organic group may have a substituent. Examples of the substituent include an alkyl group (which may be either linear or branched, preferably having 1 to 12 carbon atoms), a cycloalkyl group (which may be any of a monocycle and a polycycle (also including a spirocycle and the like), and preferably has 3 to 20 carbon atoms), an aryl group (preferably having 6 to 14 carbon atoms), a hydroxyl group, an alkoxy group, an ester group, an amido group, a urethane group, a ureido group, a thioether group, a sulfonamido group, and a sulfonic ester group. Incidentally, the carbon constituting the cyclic organic group (carbon contributing to ring formation) may be carbonyl carbon.

As the anion represented by General Formula (3), $SO_3^-$—$CF_2$—$CH_2$—OCO-(L)q'-W, $SO_3^-$—$CF_2$—CHF—$CH_2$—OCO-(L)q'-W, $SO_3^-$—$CF_2$—$O_3O$-(L)q'-W, $SO_3^-$—$CF_2$—$CF_2$—$CH_2$—$CH_2$-(L)q-W, or $SO_3^-$—$CF_2$—$CH(CF_3)$—OCO-(L)q'-W is preferable. Here, L, q, and W are each the same as in General Formula (3). q' represents an integer of 0 to 10.

In one aspect, as Z— in General Formula (Z1), Z— in General Formula (ZII), Zc- in General Formula (Z1-3b), and Z— in General Formula (Z1-4b), an anion represented by General Formula (4) is also preferable.

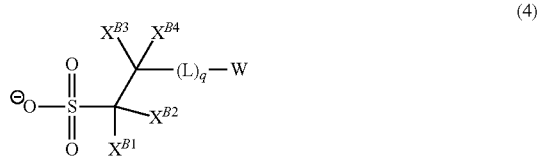

In General Formula (4), $X^{B1}$ and $X^{B2}$ each independently represent a hydrogen atom or a monovalent organic group having no fluorine atom. $X^{B1}$ and $X^{B2}$ are each preferably the hydrogen atom.

$X^{B3}$ and $X^{B4}$ each independently represent a hydrogen atom or a monovalent organic group. It is preferable that at least one of $X^{B3}$ or $X^{B4}$ is a fluorine atom or a monovalent organic group having a fluorine atom, and it is more preferable that both $X^{B3}$ and $X^{B4}$ are fluorine atoms or monovalent organic groups having a fluorine atom. It is still more preferable that both $X^{B3}$ and $X^{B4}$ are fluorine-substituted alkyl groups.

L, q, and W are the same as in General Formula (3).

As $Z^-$ in General Formula (ZI), $Z^-$ in General Formula (ZII), $Zc^-$ in General Formula (ZI-3b), and $Z^-$ in General Formula (ZI-4b), an anion represented by General Formula (5) is also preferable.

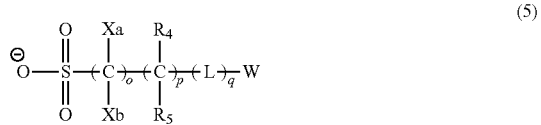

In General Formula (5), Xa's each independently represent a fluorine atom or an alkyl group substituted with at least one fluorine atom. Xb's each independently represent a hydrogen atom or an organic group having no fluorine atom. The definitions and preferred aspects of o, p, q, $R_4$, $R_5$, L, and W are each the same as those in General Formula (3).

$Z^-$ in General Formula (ZI), $Z^-$ in General Formula (ZII), $Zc^-$ in General Formula (ZI-3b), and $Z^-$ in General Formula (ZI-4b) may be a benzenesulfonate anion, and are each preferably a benzenesulfonate anion substituted with a branched alkyl group or a cycloalkyl group.

As $Z^-$ in General Formula (ZI), $Z^-$ in General Formula (ZII), $Zc^-$ in General Formula (ZI-3b), and $Z^-$ in General Formula (ZI-4b), an aromatic sulfonate anion represented by General Formula (SA1) is also preferable.

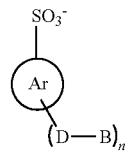

In Formula (SA1),

Ar represents an aryl group, and may further have a substituent other than a sulfonate anion and a -(D-B) group. Examples of the substituent which may be further contained include a fluorine atom and a hydroxyl group.

n represents an integer of 0 or more. n is preferably 1 to 4, more preferably 2 or 3, and still more preferably 3.

D represents a single bond or a divalent linking group. Examples of the divalent linking group include an ether group, a thioether group, a carbonyl group, a sulfoxide group, a sulfonic acid group, a sulfonate ester group, an ester group, and a group formed by combination of two or more thereof.

B represents a hydrocarbon group.

Preferably, D is a single bond and B is an aliphatic hydrocarbon structure. It is more preferable that B is an isopropyl group or a cyclohexyl group.

As $Z^-$ in General Formula (ZI), $Z^-$ in General Formula (ZII), $Zc^-$ in General Formula (ZI-3b), and $Z^-$ in General Formula (ZI-4b), a trisulfone carbanion or a disulfonamide anion is also preferable.

The trisulfone carbanion is, for example, an anion represented by $C^-(SO_2$—$R^q)_3$.

Here, $R^q$ represents an alkyl group which may have a substituent, and is preferably a fluoroalkyl group, more preferably a perfluoroalkyl group, and still more preferably a trifluoromethyl group.

The disulfonamide anion is, for example, an anion represented by $N^-(SO_2$—$R^q)_2$.

Here, $R^q$ represents an alkyl group which may have a substituent, and is preferably a fluoroalkyl group, and more preferably a perfluoroalkyl group. Two of Rq's may be bonded to each other to form a ring. A group formed by the mutual bonding of two of Rq's is preferably an alkylene group which may have a substituent, preferably a fluoroalkylene group, and more preferably a perfluoroalkylene group. The alkylene group (preferably fluoroalkylene group, and more preferably perfluoroalkylene group) preferably has 2 to 4 carbon atoms.

Preferred examples of the sulfonium cation in General Formula (ZI) and the iodonium cation in General Formula (ZII) are shown below.

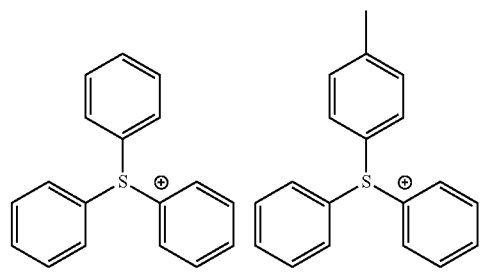

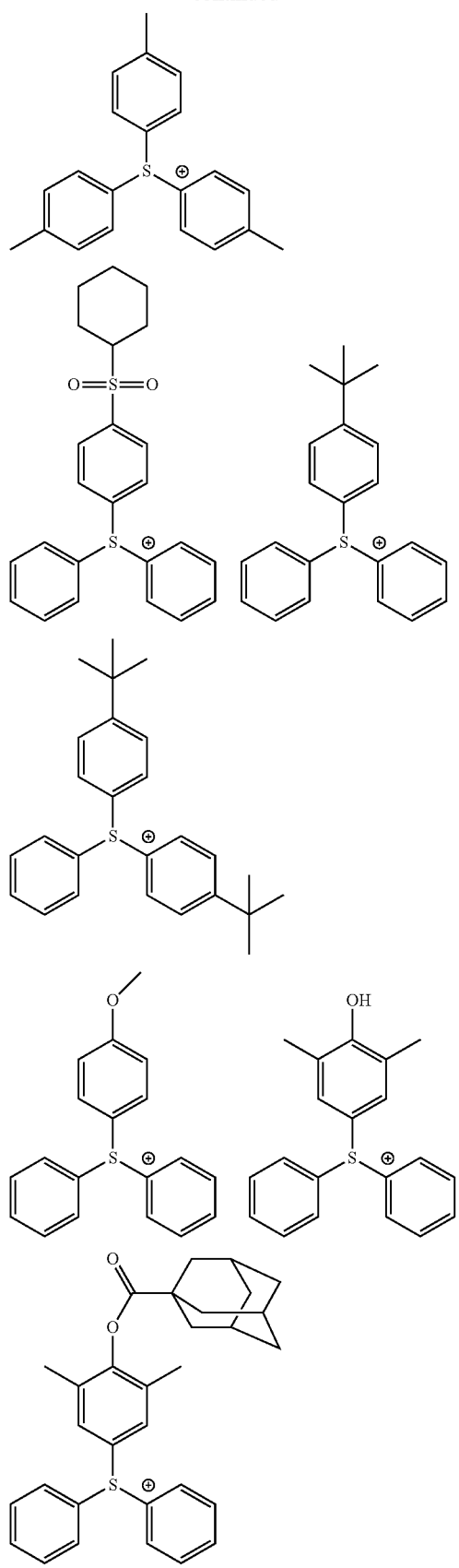
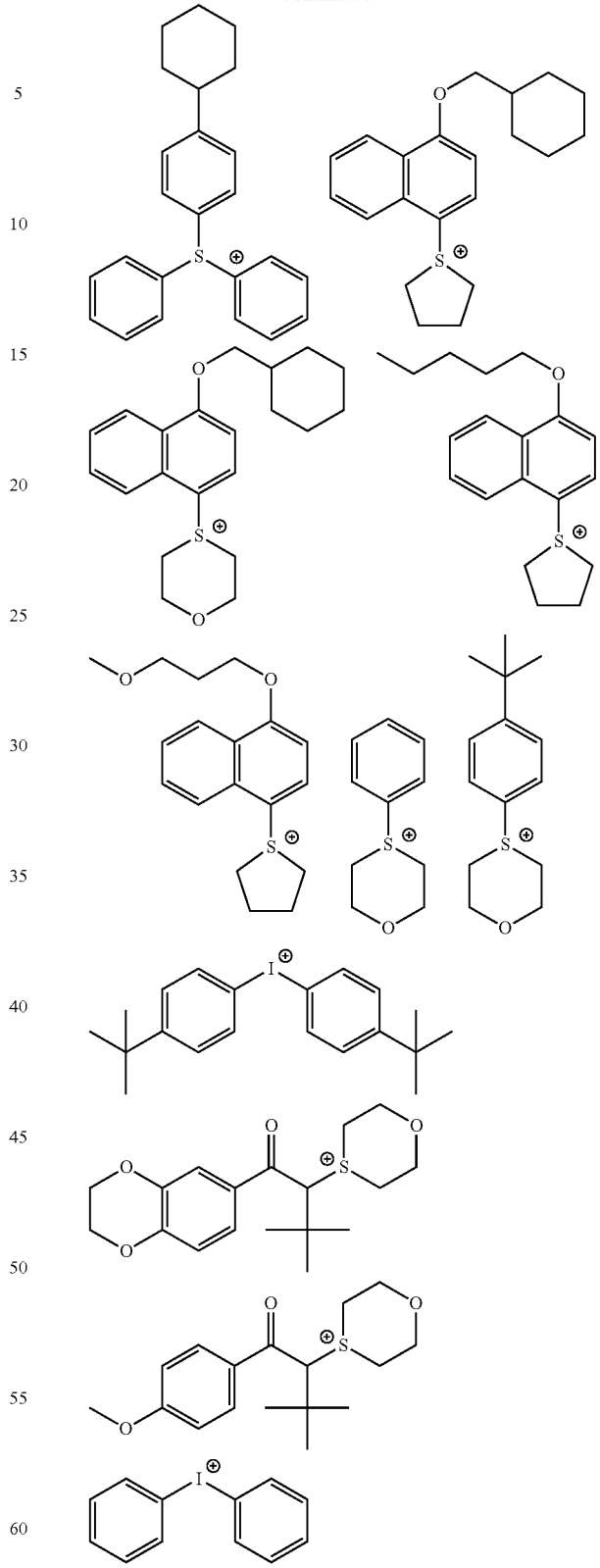
Preferred examples of the anion $Z^-$ in each of General Formula (ZI) and General Formula (ZII), $Zc^-$ in General Formula (ZI-3b), and $Z^-$ in General Formula (ZI-4b) are shown below.

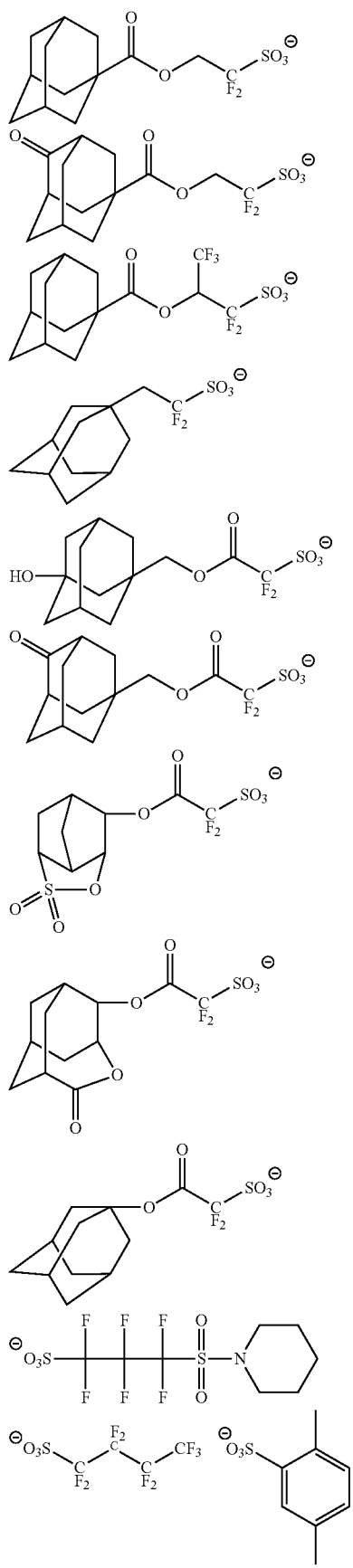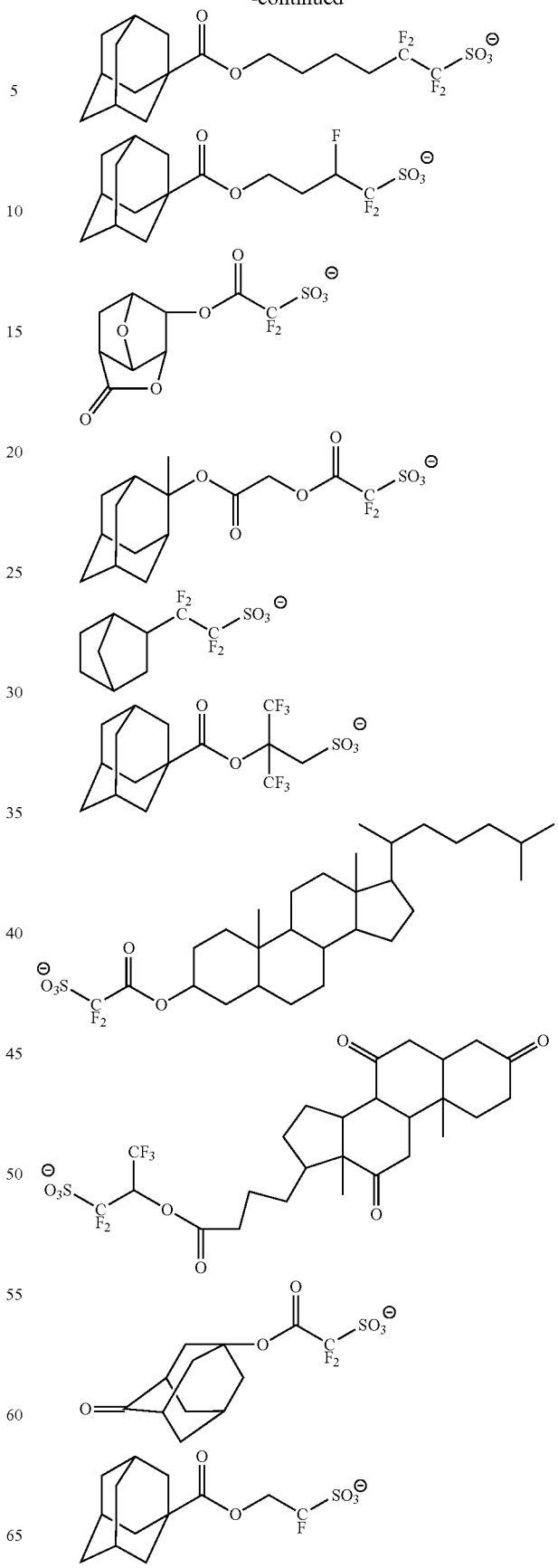

-continued

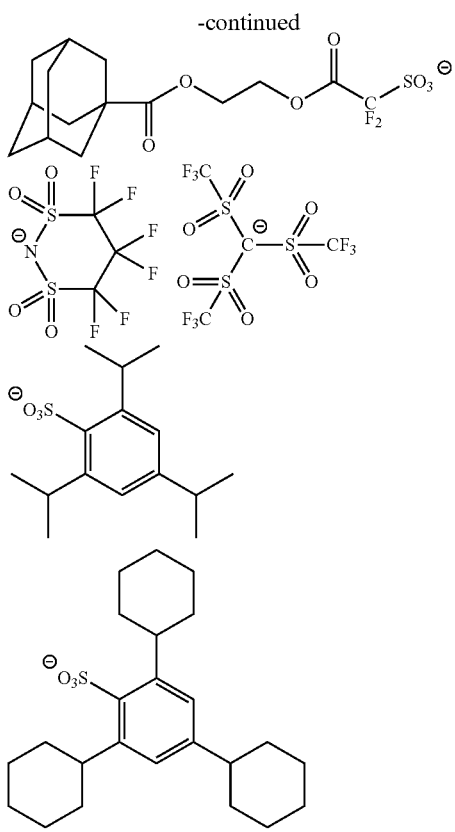

Any combination of the cations and the anions can be used as such another photoacid generator.

Such another photoacid generator may be in a form of a low-molecular-weight compound or a form incorporated into a part of a polymer. Further, a combination of the form of a low-molecular-weight compound and the form incorporated into a part of a polymer may also be used.

Such another photoacid generator is preferably in the form of a low-molecular-weight compound.

In a case where such another photoacid generator is in the form of a low-molecular-weight compound, the molecular weight is preferably 3,000 or less, more preferably 2,000 or less, and still more preferably 1,000 or less. The lower limit is not particularly limited, but is usually 50 or more.

In a case where such another photoacid generator is incorporated into a part of a polymer, it may be incorporated into a part of the resin A or into a resin other than the resin A.

The pka of an acid generated from such another photoacid generator upon irradiation with actinic rays or radiation is preferably 1.0 or less, more preferably 0.5 or less, and still more preferably 0 or less. Such another photoacid generator may be used singly or in combination of two or more kinds thereof.

A content of such another photoacid generator (in a case where such the photoacid generators are present in a plural number, a total content thereof) in the composition is preferably 0.1% to 35% by mass, more preferably 0.5% to 25% by mass, and still more preferably 2% to 5% by mass, with respect to a total solid content of the composition.

In addition, in a case where the specific photoacid generator and a photoacid generator other than the specific photoacid generator are used in combination, a total content thereof is preferably 0.1% to 35% by mass, more preferably 0.5% to 25% by mass, still more preferably 5% to 20% by mass, and particularly preferably 7.5% to 13% by mass, with respect to the total solid content of the composition.

<Acid Diffusion Control Agent>

The composition of the embodiment of the present invention preferably includes an acid diffusion control agent. The acid diffusion control agent acts as a quencher that suppresses a reaction of the acid-decomposable resin in the unexposed portion by excessive generated acids by trapping the acids generated from an acid generator and the like upon exposure. For example, a basic compound (DA), a basic compound (DB) whose basicity is reduced or lost upon irradiation with actinic rays or radiation, a low-molecular-weight compound (DD) having a nitrogen atom and a group that leaves by the action of an acid, or the like can be used as the acid diffusion control agent.

Among those, it is preferable that the composition includes the basic compound (DB) whose basicity is reduced or lost upon irradiation with actinic rays or radiation.

In the composition of the embodiment of the present invention, a known acid diffusion control agent can be appropriately used. For example, the known compounds disclosed in paragraphs [0627] to [0664] of the specification of US2016/0070167A1, paragraphs [0095] to [0187] of the specification of US2015/0004544A1, paragraphs [0403] to [0423] of the specification of US2016/0237190A1, and paragraphs [0259] to [0328] of the specification of US2016/0274458A1 can be suitably used as the acid diffusion control agent.

(Basic Compound (DA))

As the basic compound (DA), compounds having structures represented by Formulae (A) to (E) are preferable.

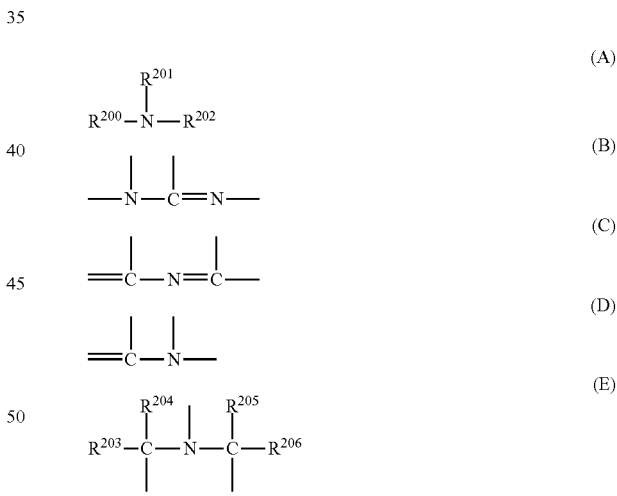

In General Formulae (A) and (E), $R^{200}$, $R^{201}$, and $R^{202}$ may be the same as or different from each other, and each independently represent a hydrogen atom, an alkyl group (preferably having 1 to 20 carbon atoms), a cycloalkyl group (preferably having 3 to 20 carbon atoms), or an aryl group (preferably having 6 to 20 carbon atoms). $R^{201}$ and $R^{202}$ may be bonded to each other to form a ring.

$R^{203}$, $R^{204}$, $R^{205}$, and $R^{206}$ may be the same as or different from each other and each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl groups in each of General Formulae (A) and (E) are more preferably unsubstituted.

As the basic compound (DA), guanidine, aminopyrrolidine, pyrazole, pyrazoline, piperazine, aminomorpholine, aminoalkylmorpholine, piperidine, or the like is preferable; and a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, and an aniline derivative having a hydroxyl group and/or an ether bond, or the like is more preferable.

(Basic compound (DB) whose Basicity Is Reduced or Lost upon Irradiation with Actinic Rays or Radiation)

The basic compound (DB) whose basicity is reduced or lost upon irradiation with actinic rays or radiation (hereinafter also referred to as a "compound (DB)") is a compound which is different from the photoacid generator represented by General Formula (b1).

The compound (DB) is a compound that decomposes upon irradiation (exposure) with actinic rays or radiation to generate a compound (acid) with reduced basicity. The compound with reduced basicity is, for example, a conjugate acid of compound (DB).

The pka of an acid generated from the compound (DB) is, for example, preferably more than 0.5, more preferably more than 1.0, and still more preferably more than 1.5.

Furthermore, in a case where the compound (DB) has an anion represented by General Formula (c-1), the pka of the acid generated from the compound (DB) is also preferably more than −11.0, for example.

Moreover, the compound (DB) also preferably has, for example, a proton-accepting functional group.

The proton-accepting functional group refers to a functional group having a group or an electron which is capable of electrostatically interacting with a proton, and for example, means a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following formula.

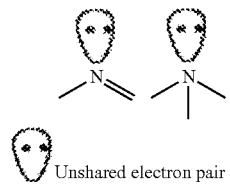
Unshared electron pair

Preferred examples of the partial structure of the proton-accepting functional group include a crown ether structure, an azacrown ether structure, primary to tertiary amine structures, a pyridine structure, an imidazole structure, and a pyrazine structure.

The compound (DB) preferably decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease in the equilibrium constant at chemical equilibrium in a case where a proton adduct is generated from the compound (DB) having the proton-accepting functional group and the proton.

The proton-accepting properties can be confirmed by performing pH measurement.

The compound (DB) is preferably an onium salt compound consisting of an anion and a cation. Examples of such an onium salt compound include a compound constituted with a combination of an anion and a cation described below.

Anion

A preferred aspect will be described as the anion contained in the compound (DB) which is an onium salt compound consisting of an anion and a cation. In other words, the acid diffusion control agent is preferably a compound having an anion described below.

As the anion contained in the compound (DB) which is an onium salt compound consisting of an anion and a cation, for example, anions represented by General Formulae (d1-1) to (d1-3) are preferable.

In the formula, $R^{51}$ represents a hydrocarbon group which may have a substituent.

$Z^{2c}$ represents a hydrocarbon group having 1 to 30 carbon atoms which may have a substituent (provided that carbon adjacent to S is not substituted with a fluorine atom).

$R^{52}$ represents an organic group, $Y^3$ represents a linear, branched, or cyclic alkylene group or an arylene group, and Rf represents a hydrocarbon group including a fluorine atom.

The anion contained in the compound (DB), which is an onium salt compound consisting of an anion and a cation, is also preferably an anion represented by General Formula (c-1).

That is, the compound (DB) is also preferably a compound having the anion represented by General Formula (c-1).

In General Formula (c-1),
Q represents —SO$_3^-$, —OO$_2^-$, or —W$_1$—N$^-$—W$_2$R$_f$.
W$_1$ and W$_2$ each independently represent —SO$_2$— or —CO—.
R$_f$ represents an alkyl group which may have a substituent, a cycloalkyl group which may have a substituent, or an aryl group which may have a substituent.

A represents a single bond or a divalent linking group.

X represents a single bond, —$SO_2$—, or —CO—.

B represents a single bond, an oxygen atom, or —N($R_x$)$R_y$—.

$R_x$ represents a hydrogen atom or an organic group.

$R_y$ represents a single bond or a divalent organic group.

R represents a monovalent organic group having a proton-accepting functional group.

$R_x$ may be bonded to $R_y$ to form a ring, and may be bonded to R to form a ring.

It is preferable that at least one of $W_1$ or $W_2$ is —$SO_2$—, and it is more preferable that both are —$SO_2$—.

Rf is preferably an alkyl group having 1 to 6 carbon atoms, which may have a fluorine atom, more preferably a perfluoroalkyl group having 1 to 6 carbon atoms, and a perfluoroalkyl group having 1 to 3 carbon atoms.

The divalent linking group for A is preferably a divalent linking group having 2 to 12 carbon atoms, and examples thereof include an alkylene group and a phenylene group. Among those, an alkylene group having at least one fluorine atom is preferable, and the alkylene group preferably has 2 to 6 carbon atoms, and more preferably has 2 to 4 carbon atoms. The alkylene chain may have a linking group such as an oxygen atom or a sulfur atom. The alkylene group is preferably an alkylene group in which 30% to 100% of the hydrogen atoms have been substituted with fluorine atoms, and more preferably an alkylene group in which the carbon atom bonded to the Q site has a fluorine atom. Among those, the divalent linking group for A is preferably a perfluoroalkylene group, and more preferably a perfluoroethylene group, a perfluoropropylene group, or a perfluorobutylene group.

The monovalent organic group for Rx preferably has 2 to 30 carbon atoms, and examples thereof include an alkyl group, a cycloalkyl group which may have an oxygen atom in the ring, an aryl group, an aralkyl group, and an alkenyl group.

The alkyl group for Rx may have a substituent, and is preferably a linear or branched alkyl group having 1 to 20 carbon atoms, and an oxygen atom, a sulfur atom, and/or a nitrogen atom may be contained in the alkyl chain.

Furthermore, examples of the alkyl group having a substituent include a linear or branched alkyl group substituted with a cycloalkyl group (for example, an adamantylmethyl group, an adamantylethyl group, a cyclohexylethyl group, and a camphor residue).

The cycloalkyl group for Rx may have a substituent and is preferably a cycloalkyl group having 3 to 20 carbon atoms. Further, the cycloalkyl group may have an oxygen atom in the ring.

The aryl group for Rx may have a substituent, and is preferably an aryl group having 6 to 14 carbon atoms.

The aralkyl group for Rx may have a substituent, and is preferably an aralkyl group having 7 to 20 carbon atoms.

The alkenyl group for Rx may have a substituent, and examples thereof include a group having a double bond at any position of the alkyl group mentioned as Rx.

In a case where B represents —N(Rx)Ry-, the divalent organic group for Ry is preferably an alkylene group. Further, in this case, examples of the ring structure formed by the mutual bonding of Rx and Ry include a 5- to 8-membered ring including a nitrogen atom, and particularly preferably a 6-membered ring.

In a case where B represents —N(Rx)Ry-, it is preferable that R and Rx are bonded to each other to form a ring. By forming a ring structure, stability is improved, and the storage stability of a composition using the same ring structure is improved. The number of carbon atoms forming the ring is preferably 4 to 20 and may be either a monocycle or a polycycle, and the ring may include an oxygen atom, a sulfur atom and/or a nitrogen atom.

Examples of the monocycle include a 4-membered ring, a 5-membered ring, a 6-membered ring, a 7-membered ring, and an 8-membered ring, each of which includes a nitrogen atom. Examples of such a ring structure include a piperazine ring and a piperidine ring. The polycycle includes a structure constituted with a combination of 2 or 3 or more monocyclic structures. Each of the monocycle and the polycycle may have a substituent, which is preferably a halogen atom, a hydroxyl group, a cyano group, a carboxy group, a carbonyl group, a cycloalkyl group (preferably having 3 to 10 carbon atoms), an aryl group (preferably having 6 to 14 carbon atoms), an alkoxy group (preferably having 1 to 10 carbon atoms), an acyl group (preferably having 2 to 15 carbon atoms), an acyloxy group (preferably having 2 to 15 carbon atoms), an alkoxycarbonyl group (preferably having 2 to 15 carbon atoms), and aminoacyl group (preferably 2 to 20 carbon atoms). These substituents may have a substituent where available. In a case where the aryl group and the cycloalkyl group each further have a substituent, examples of the substituent include an alkyl group (preferably having 1 to 15 carbon atoms). Examples of the substituent which may be further contained in the aminoacyl group include an alkyl group (preferably having 1 to 15 carbon atoms).

The proton-accepting functional group in R is as described above, and preferred examples of a partial structure thereof include structures of a crown ether, primary to tertiary amines, and a nitrogen-containing heterocycle (pyridine, imidazole, pyrazine, and the like).

Furthermore, as the proton-accepting functional group, a functional group having a nitrogen atom is preferable, and a group having a primary to tertiary amino group or a nitrogen-containing heterocyclic group is more preferable. In these structures, it is preferable that all of the atoms adjacent to the nitrogen atom included in the structure are carbon atoms or hydrogen atoms. In addition, it is preferable that an electron-withdrawing functional group (such as a carbonyl group, a sulfonyl group, a cyano group, and a halogen atom) is not directly linked to the nitrogen atom.

The monovalent organic group in the monovalent organic group (the group R) including such a proton-accepting functional group preferably has 2 to 30 carbon atoms, examples thereof include an alkyl group, a cycloalkyl group, an aryl group, an aralkyl group, and an alkenyl group, and each of the groups may have a substituent.

In the alkyl group, the cycloalkyl group, the aryl group, the aralkyl group, and the alkenyl group, each including a proton-accepting functional group in R, the alkyl group, the cycloalkyl group, the aryl group, the aralkyl group, and the alkenyl group are the same as the alkyl group, the cycloalkyl group, the aryl group, the aralkyl group, and the alkenyl group mentioned as Rx, respectively.

Examples of the substituent which may be contained in each of the groups include a halogen atom, a hydroxyl group, a nitro group, a cyano group, a carboxyl group, a cycloalkyl group (preferably having 3 to 10 carbon atoms, a part of which may be substituted with a heteroatom or a group having a heteroatom (an ester group and the like)), an aryl group (preferably having 6 to 14 carbon atoms), an alkoxy group (preferably having 1 to 10 carbon atoms), an acyl group (preferably having 2 to 20 carbon atoms), an acyloxy groups (preferably having 2 to 10 carbon atoms), an alkoxycarbonyl groups (preferably having 2 to 20 carbon atoms), and an aminoacyl groups (preferably having 2 to 20 carbon atoms). Examples of the substituent which may be contained in the cyclic group in the aryl group, the cycloalkyl group, and the like include an alkyl group (preferably having 1 to 20 carbon atoms). Examples of the substituent contained in the aminoacyl group include 1 or 2 alkyl groups (preferably having 1 to 20 carbon atoms).

Cation

Examples of the cation contained in the compound (DB) which is an onium salt compound consisting of an anion and a cation include the cations (more specifically a portion other than $Z^-$ in General Formula (ZI), a portion other than $Z^-$ in General Formula (ZII), a portion other than $Zc^-$ in General Formula (ZI-3b), and a portion other than $Z^-$ in General Formula (ZI-4b)) described above as the cation which may be contained in the compounds represented by General Formula (ZI) and General Formula (ZII).

Furthermore, in the compound (DB) which is an onium salt compound consisting of an anion and a cation, the cation is preferably a cation having a basic moiety including a nitrogen atom. The basic moiety is preferably an amino group, and more preferably an aliphatic amino group. All of the atoms adjacent to the nitrogen atom in the basic moiety are still more preferably hydrogen atoms or carbon atoms. Further, from the viewpoint of improving basicity, it is preferable that an electron-withdrawing functional group (such as a carbonyl group, a sulfonyl group, a cyano group, and a halogen atom) is not directly linked to the nitrogen atom.

Specific structures of such the cation include, but are not limited to, the cations in the compounds disclosed in paragraph [0203] of the specification of US2015/0309408A1.

The compound (DB) may be a compound in which a cationic group and an anionic group are contained in the same molecule, and the cationic group and anionic group are linked through a covalent bond (hereinafter also referred to as a "compound (DCA)").

The compound (DCA) is preferably a compound represented by any of General Formulae (C-1) to (C-3).

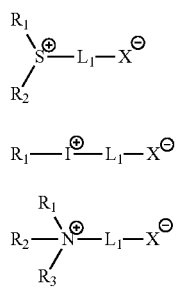

In General Formulae (C-1) to (C-3), $R_1$, $R_2$, and $R_3$ each independently represent a substituent having 1 or more carbon atoms.

$L_1$ represents a divalent linking group or a single bond that links a cationic group ($S^+$, $I^+$, or $N^+$) with $-X^+$.

$-X^-$ represents $-COO^-$, $-SO_3^-$, $-SO_2^-$, or $-N^-$—$R_4$.

$R_4$ represents a monovalent substituent having at least one of a carbonyl group ($-CO-$), a sulfonyl group ($-SO_2-$), or a sulfinyl group: $-S(=O)-$ at a site for linking to an adjacent N atom.

$R_1$, $R_2$, $R_3$, $R_4$, and $L_1$ may be bonded to each other to form a ring. It should be noted that the ring formed by the mutual bonding of $R_1$ and $R_2$ in General Formula (C-1) does not have a heteroatom other than $S^+$.

Further, in General Formula (C-3), two of $R_1$ to $R_3$ together represent one divalent substituent, and may be bonded to an N atom through a double bond.

Examples of the substituent having 1 or more carbon atoms in each of $R_1$ to $R_3$ include an alkyl group, a cycloalkyl group, an aryl group (preferably having 6 to 15 carbon atoms), an alkyloxycarbonyl group, a cycloalkyloxycarbonyl group, an aryloxycarbonyl group, an alkylaminocarbonyl group, a cycloalkylaminocarbonyl group, and an arylaminocarbonyl group. Among those, an alkyl group, a cycloalkyl group, or an aryl group is preferable.

Examples of $L_1$ as a divalent linking group include a linear or branched alkylene group, a cycloalkylene group, an arylene group (preferably having 6 to 15 carbon atoms), a carbonyl group, an ether bond, an ester bond, an amide bond, an urethane bond, an urea bond, and a group formed by a combination of two or more of these groups. Among those, the alkylene group, the arylene group, the ether bond, the ester bond, or the group formed by a combination of two or more of these groups is preferable.

(Low-Molecular Weight Compound (DD) Having Nitrogen Atom and Group That Leaves by Action of Acid)

The low-molecular-weight compound (DD) having a nitrogen atom and having a group that leaves by the action of an acid (hereinafter also referred to as a "compound (DD)") is preferably an amine derivative having a group that leaves by the action of an acid on the nitrogen atom.

As the group that leaves by the action of an acid, an acetal group, a carbonate group, a carbamate group, a tertiary ester group, a tertiary hydroxyl group, or a hemiaminal ether group is preferable, and the carbamate group or the hemiaminal ether group is more preferable.

The molecular weight of the compound (DD) is preferably 100 to 1,000, more preferably 100 to 700, and still more preferably 100 to 500.

The compound (DD) may have a carbamate group having a protective group on the nitrogen atom. The protective group constituting the carbamate group is represented by General Formula (d-1).

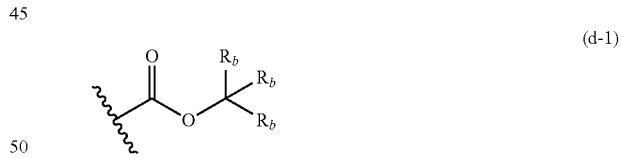

In General Formula (d-1),

Rb is independently a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably 1 to 10 carbon atoms). Rb's may be linked to each other to form a ring.

The alkyl group, a cycloalkyl group, aryl group, and aralkyl group represented by Rb may be each independently substituted with a hydroxyl group, a cyano group, an amino group, a pyrrolidino group, a piperidino group, a morpholino group, an oxo group, or another functional group, an alkoxy group, or a halogen atom. The same applies to the alkoxyalkyl group represented by Rb.

Rb is preferably a linear or branched alkyl group, a cycloalkyl group, or an aryl group, and more preferably the linear or branched alkyl group, or the cycloalkyl group.

Examples of the ring formed by the mutual linking of two of Rb's include an alicyclic hydrocarbon group, an aromatic hydrocarbon group, a heterocyclic hydrocarbon group, and derivatives thereof.

Examples of the specific structure of the group represented by General Formula (d-1) include, but are not limited to, the structures disclosed in paragraph [0466] of the specification of US2012/0135348A1.

The compound (DD) preferably has a structure represented by General Formula (6).

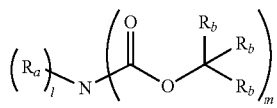
(6)

In General Formula (6), l represents an integer of 0 to 2, m represents an integer of 1 to 3, and these satisfy l+m=3.

Ra represents a hydrogen atom, an alkyl group, a cycloalkyl group, an aryl group, or an aralkyl group. In a case where l is 2, two of Ra's may be the same as or different from each other, and the two of Ra's may be linked to each other to form a heterocycle with the nitrogen atom in the formula. This heterocycle may include a heteroatom other than the nitrogen atom in the formula.

Rb has the same meaning as Rb in General Formula (d-1), and preferred examples are also the same.

In General Formula (6), the alkyl group, the cycloalkyl group, the aryl group, and the aralkyl group as Ra may be substituted with the same groups as the group mentioned above as a group which may be each independently substituted in the alkyl group, the cycloalkyl group, the aryl group, and the aralkyl group as Rb.

Specific examples of the alkyl group, the cycloalkyl group, the aryl group, and the aralkyl group (such the alkyl group, the cycloalkyl group, the aryl group, and the aralkyl group may be substituted with the groups as described above) of Ra include the same groups as the specific examples as described above with respect to Rb.

Specific structures of the particularly preferred compound (DD) in the present invention include, but are not limited to, the compounds disclosed in paragraph [0475] of the specification of US2012/0135348A1.

The acid diffusion control agent is exemplified below.

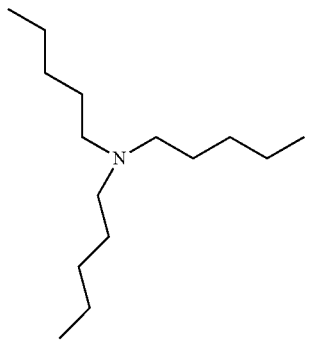

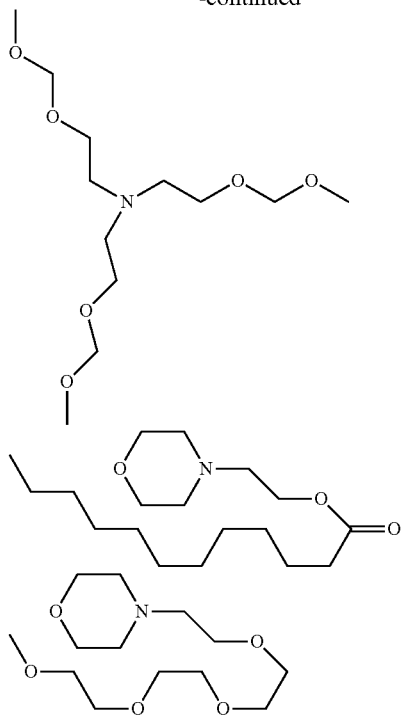

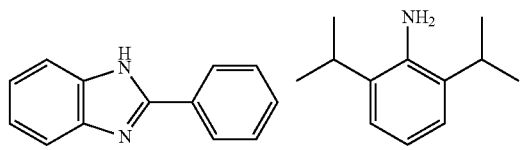

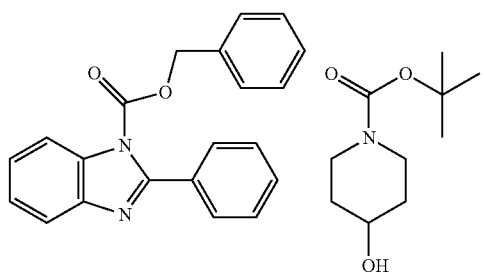

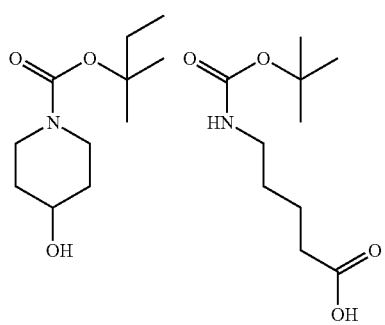

51
-continued
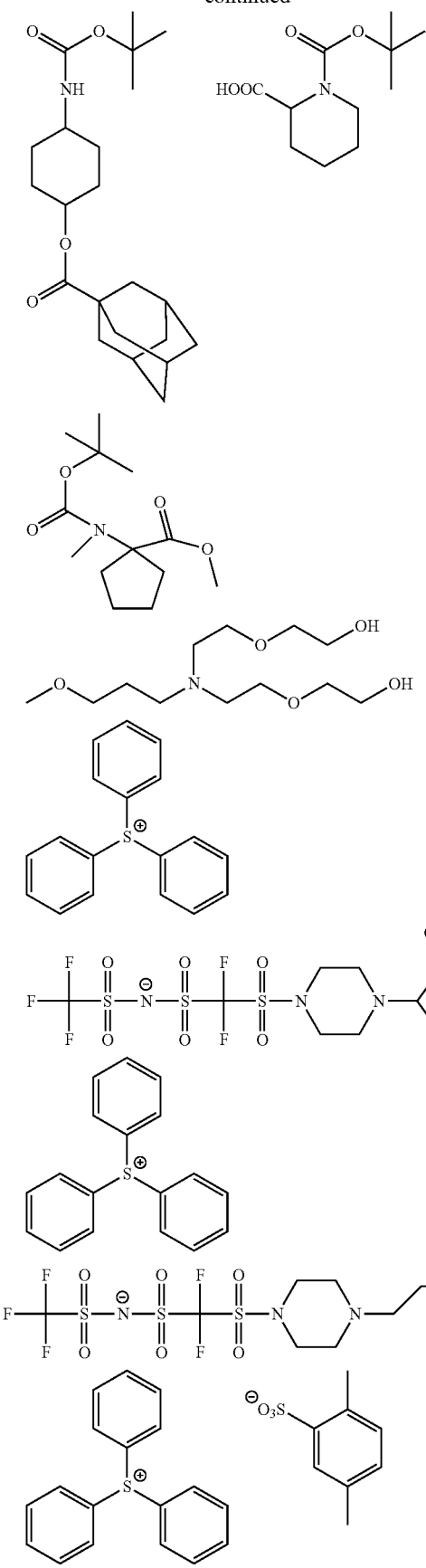
52
-continued
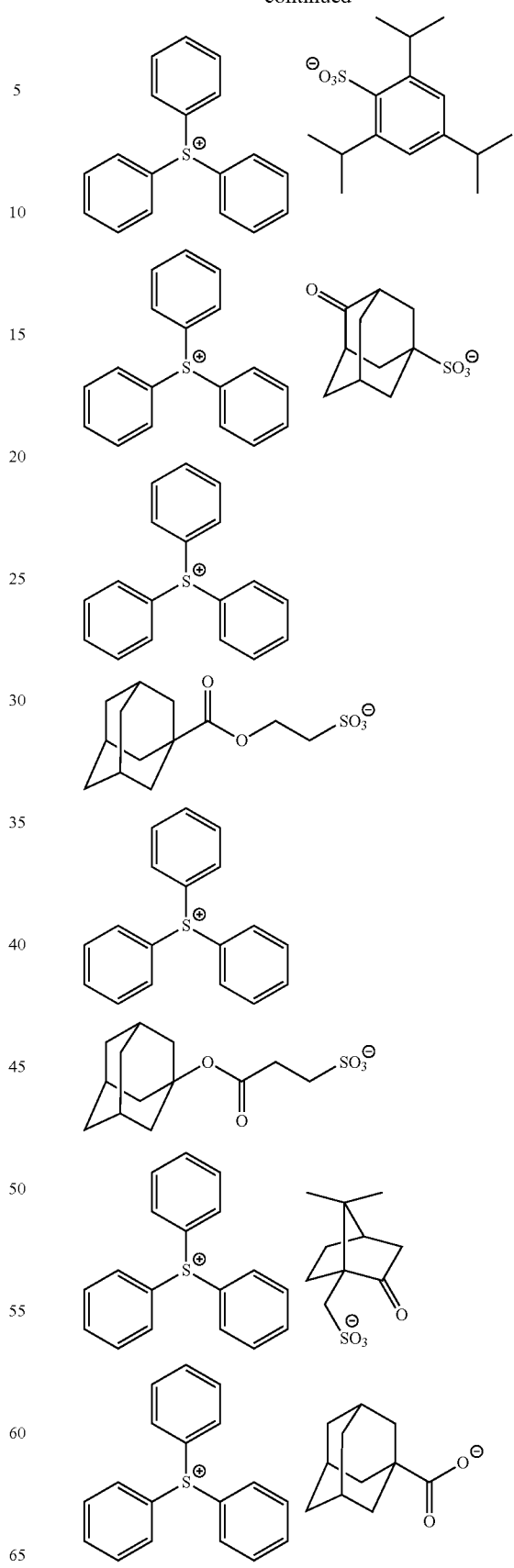

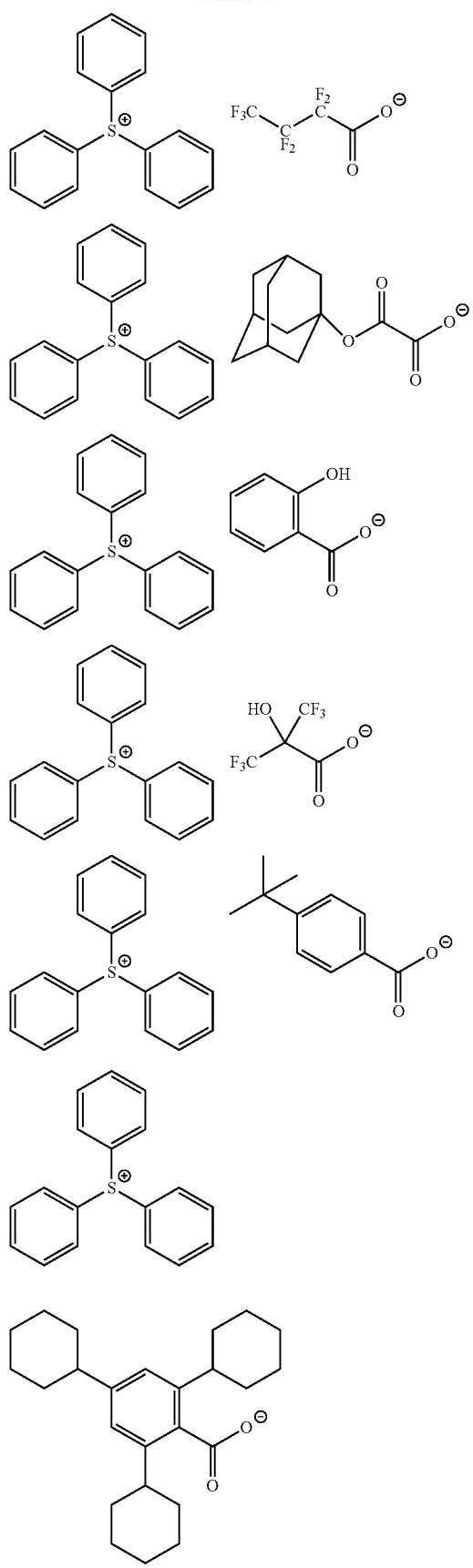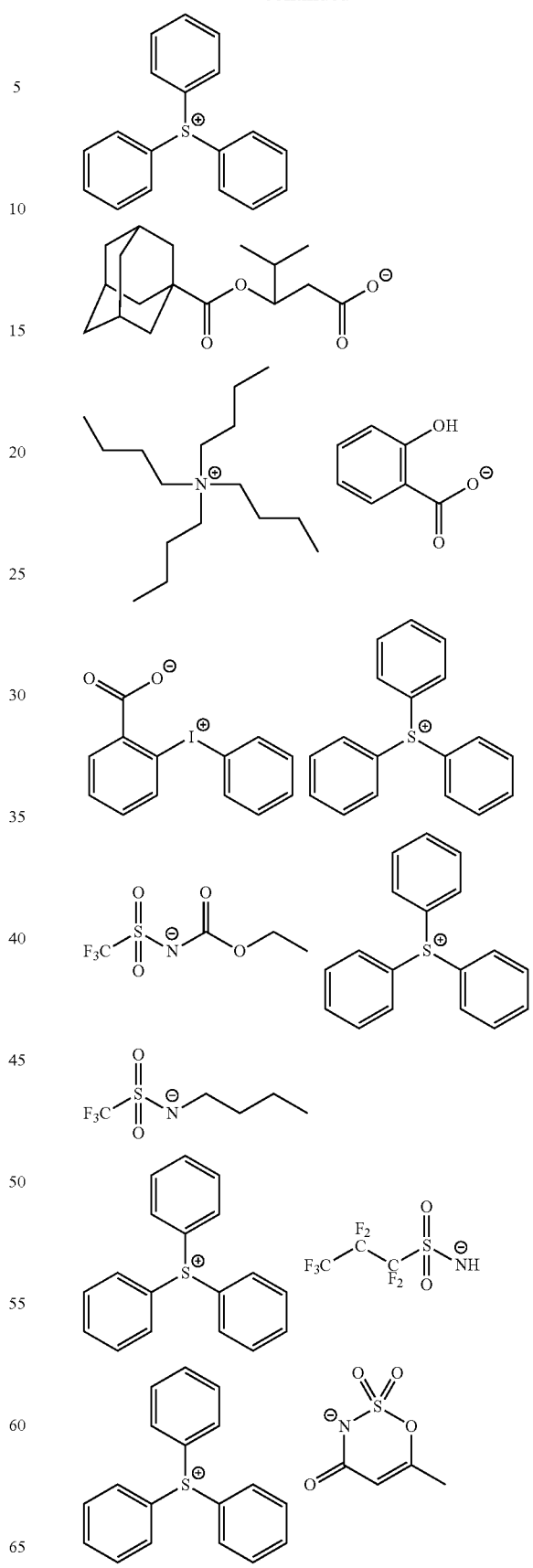

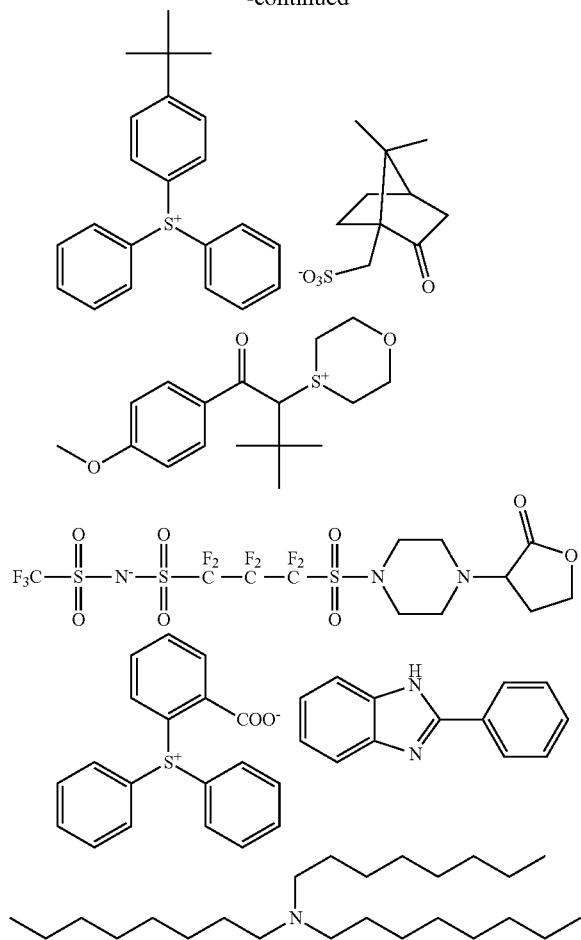

In the composition of the embodiment of the present invention, the acid diffusion control agents may be used singly or in combination of two or more kinds thereof.

The content of the acid diffusion control agent (in a case where the acid diffusion control agents are present in a plurality of kinds, a total content thereof) in the composition is preferably 0.1% to 10% by mass, and more preferably 0.1% to 5% by mass, with respect to the total solid content of the composition.

<Hydrophobic Resin>

The composition of the embodiment of the present invention may include a hydrophobic resin. Further, the hydrophobic resin is preferably a resin different from the resin A.

By incorporation of the hydrophobic resin into the composition of the embodiment of the present invention, the static and/or dynamic contact angle on the surface of the actinic ray-sensitive or radiation-sensitive film can be controlled. Thus, it is possible to improve development characteristics, suppress generation of out gas, improve immersion liquid tracking properties upon liquid immersion exposure, and reduce liquid immersion defects, for example.

It is preferable that the hydrophobic resin is designed to be unevenly distributed on a surface of a resist film, but unlike the surfactant, the hydrophobic resin does not necessarily have a hydrophilic group in a molecule thereof and does not necessarily contribute to homogeneous mixing of polar materials and non-polar materials.

The hydrophobic resin is preferably a resin having a repeating unit having at least one selected from the group consisting of a "fluorine atom", a "silicon atom", or a "CH$_3$ partial structure which is included in a side chain portion of a resin" from the viewpoint of uneven distribution on a film surface layer.

In a case where the hydrophobic resin includes a fluorine atom and/or a silicon atom, the fluorine atom and/or the silicon atom described above in the hydrophobic resin may be included in the main chain of a resin or may be included in a side chain.

In a case where the hydrophobic resin includes a fluorine atom, it is preferably a resin which has an alkyl group having a fluorine atom, a cycloalkyl group having a fluorine atom, or an aryl group having a fluorine atom as a partial structure having a fluorine atom.

The hydrophobic resin preferably has at least one group selected from the following (x) to (z) groups:

(x) an acid group,
(y) a group whose solubility in an alkali developer increases through decomposition by the action of the alkali developer (hereinafter also referred to as a polarity converting group), and
(z) a group that decomposes by the action of an acid.

Examples of the acid group (x) include a phenolic hydroxyl group, a carboxy group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group.

As the acid group, the fluorinated alcohol group (preferably hexafluoroisopropanol), the sulfonimido group, or the bis(alkylcarbonyl)methylene group is preferable.

Examples of the group (y) whose solubility in an alkali developer increases through decomposition by the action of the alkali developer include a lactone group, a carboxyester group (—COO—), an acid anhydride group (—CO—O—CO—), an acid imido group (—NHCONH—), a carboxythioester group (—COS—), a carbonate ester group (—O—CO—O—), a sulfuric ester group (—OSO$_2$O—), and a sulfonic ester group (—SO$_2$O—), and the lactone group or the carboxyester group (—COO—) is preferable.

The repeating unit including such the group is, for example, a repeating unit in which the group is directly bonded to the main chain of a resin, and examples thereof include a repeating unit with an acrylic ester or a methacrylic ester. In this repeating unit, such the group may be bonded to the main chain of the resin via a linking group. Alternatively, this repeating unit may also be incorporated into a terminal of the resin by using a polymerization initiator or a chain transfer agent having such the group during polymerization.

Examples of the repeating unit having a lactone group include the same ones as those of the repeating unit having a lactone structure described earlier in the section of the resin A.

The content of the repeating unit having the group (y) whose solubility in an alkali developer increases through decomposition by the action of the alkali developer is preferably 1% to 100% by mole, more preferably 3% to 98% by mole, and still more preferably 5% to 95% by mole, with respect to all the repeating units in the hydrophobic resin.

Examples of the repeating unit having the group (z) that decomposes by the action of an acid in the hydrophobic resin include the same ones as the repeating units having an acid-decomposable group exemplified in the resin A. The repeating unit having a group (z) that decomposes by the action of an acid may have at least any one of a fluorine atom or a silicon atom. A content of the repeating unit having a group (z) that decomposes by the action of an acid is preferably 1% to 80% by mole, more preferably 10% to 80% by mole, and still more preferably 20% to 60% by mole, with respect to all the repeating units in the hydrophobic resin.

The hydrophobic resin may further have a repeating unit which is different from the above-mentioned repeating units.

A content of the repeating unit including a fluorine atom is preferably 10% to 100% by mole, and more preferably 30% to 100% by mole, with respect to all the repeating units in the hydrophobic resin. Further, the content of the repeating units including a silicon atom is preferably 10% to 100% by mole, and more preferably 20% to 100% by mole, with respect to all the repeating units in the hydrophobic resin.

On the other hand, in a case where the hydrophobic resin includes a $CH_3$ partial structure in the side chain portion thereof, a form in which the hydrophobic resin does not substantially include a fluorine atom and a silicon atom. Further, it is preferable that the hydrophobic resin is constituted with substantially only repeating units which are constituted with only atoms selected from a carbon atom, an oxygen atom, a hydrogen atom, a nitrogen atom, and a sulfur atom.

The weight-average molecular weight of the hydrophobic resin in terms of standard polystyrene is preferably 1,000 to 100,000, and more preferably 1,000 to 50,000.

A total content of the residual monomers and/or oligomer components included in the hydrophobic resin is preferably 0.01% to 5% by mass, and more preferably 0.01% to 3% by mass. In addition, the dispersity (Mw/Mn) is preferably 1.0 to 5.0, and more preferably 1.0 to 3.0.

As the hydrophobic resin, known resins can be appropriately selected and used singly or as a mixture. For example, the known resins disclosed in paragraphs [0451] to [0704] of the specification of US2015/0168830A1 and paragraphs [0340] to [0356] of the specification of US2016/0274458A1 can be suitably used as the hydrophobic resin. In addition, the repeating units disclosed in paragraphs [0177] to [0258] of the specification of US2016/0237190A1 are also preferable as the repeating units constituting the hydrophobic resin.

Preferred examples of a monomer corresponding to the repeating unit constituting the hydrophobic resin are shown below.

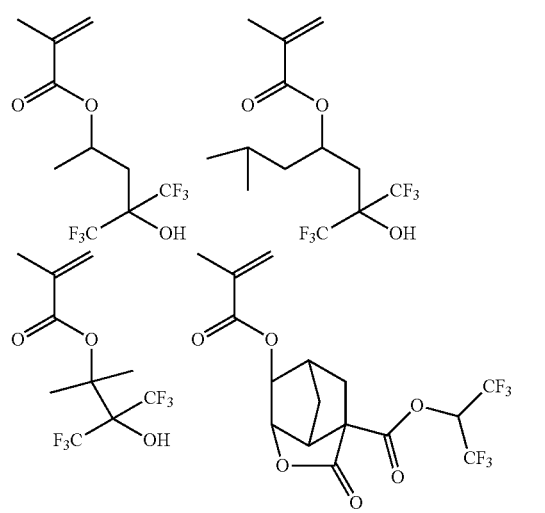

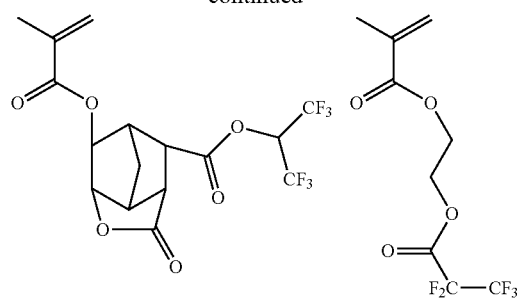

-continued

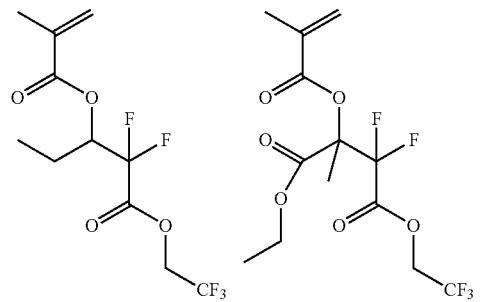

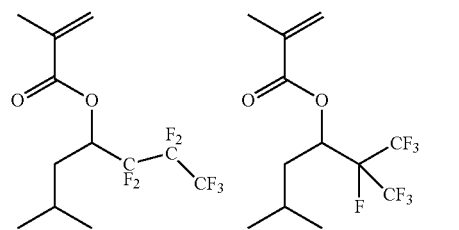

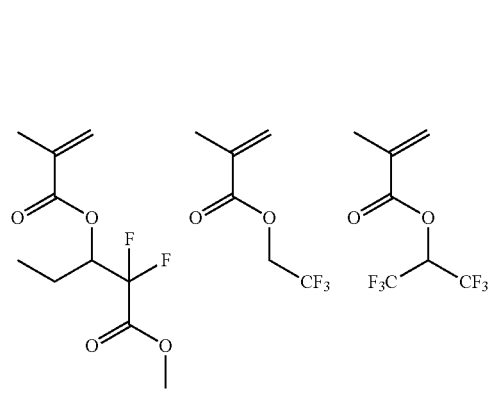

-continued

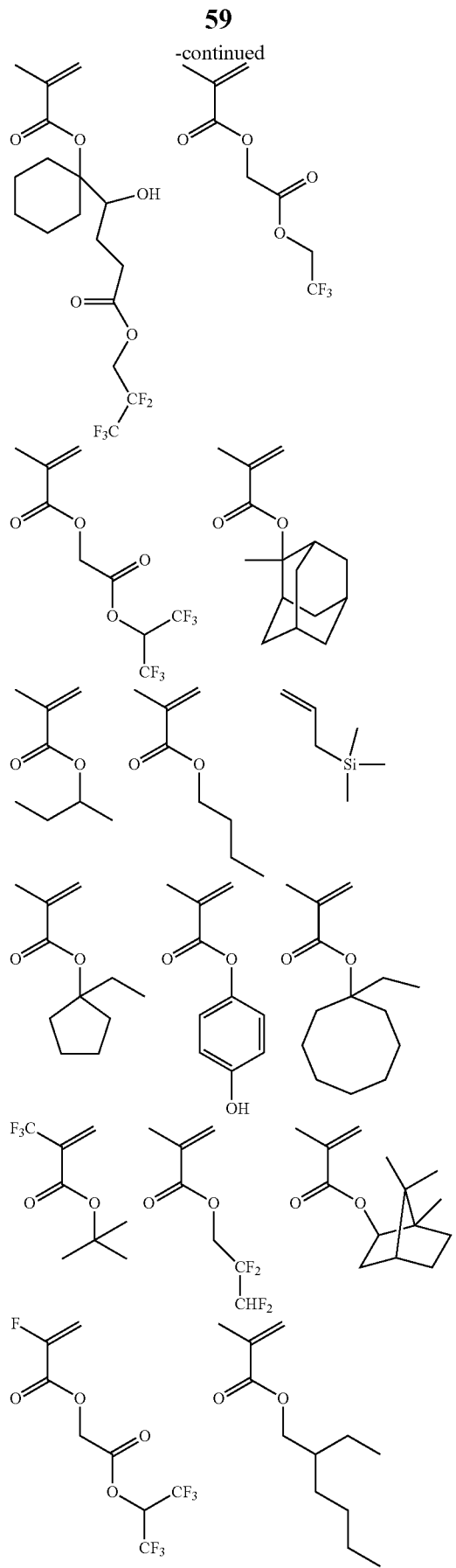

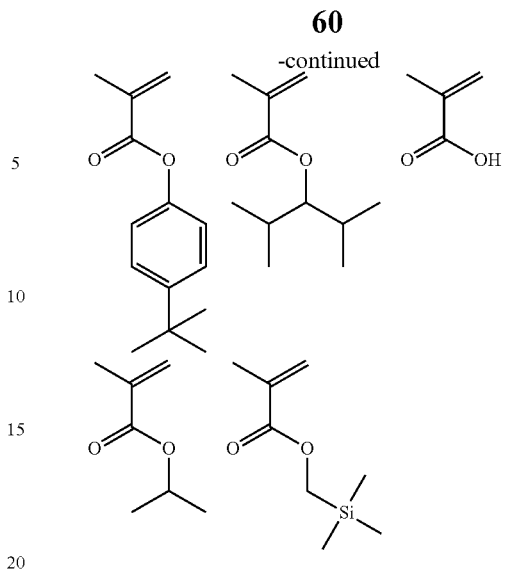

The hydrophobic resins may be used singly or in combination of two or more kinds thereof.

It is also preferable to use a mixture of two or more kinds of hydrophobic resins having different levels of surface energy from the viewpoint of satisfying both the immersion liquid tracking properties and the development characteristics upon liquid immersion exposure.

A content of the hydrophobic resin in the composition is preferably 0.01% to 10% by mass, and more preferably 0.03% to 8% by mass, with respect to the total solid content of the composition of the embodiment of the present invention.

<Solvent>

The composition of the embodiment of the present invention may include a solvent.

In the composition of the embodiment of the present invention, a known resist solvent can be appropriately used. For example, the known solvents disclosed in paragraphs [0665] to [0670] of the specification of US2016/0070167A1, paragraphs [0210] to [0235] of the specification of US2015/0004544A1, paragraphs [0424] to [0426] of the specification of US2016/0237190A1, and paragraphs [0357] to [0366] of the specification of US2016/0274458A1 can be suitably used.

Examples of the solvent which can be used in preparation of the composition include organic solvents such as alkylene glycol monoalkyl ether carboxylate, alkylene glycol monoalkyl ether, alkyl lactate ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

As the organic solvent, a mixed solvent obtained by mixing a solvent having a hydroxyl group in the structure and a solvent having no hydroxyl group may be used.

As the solvent having a hydroxyl group and the solvent having no hydroxyl group, the above-exemplified compounds can be appropriately selected, but as the solvent having a hydroxyl group, alkylene glycol monoalkyl ether or alkyl lactate is preferable, and propylene glycol monomethyl ether (PGME), propylene glycol monoethyl ether (PGEE), methyl 2-hydroxyisobutyrate, or ethyl lactate is more preferable. Further, as the solvent having no hydroxyl group, alkylene glycol monoalkyl ether acetate, alkylalkoxypropionate, a monoketone compound which may have a ring, a cyclic lactone, alkyl acetate, or the like is preferable, and among these, propylene glycol monomethyl ether acetate (PGMEA), ethyl ethoxypropionate, 2-heptanone, γ-butyrolactone, cyclohexanone, cyclopentanone, or butyl acetate is more preferable, and propylene glycol monomethyl ether acetate, γ-butyrolactone, ethyl ethoxypropionate, cyclohexanone, cyclopentanone, or 2-heptanone are more preferable. As a solvent having no hydroxyl group, propylene carbonate is also preferable.

A mixing ratio (mass ratio) of the solvent having a hydroxyl group to the solvent having no hydroxyl group is 1/99 to 99/1, preferably 10/90 to 90/10, and more preferably 20/80 to 60/40. A mixed solvent including 50% by mass or more of the solvent having no hydroxyl group is preferable from the viewpoint of coating evenness.

The solvent preferably includes propylene glycol monomethyl ether acetate. In this case, the solvent may be a single solvent of propylene glycol monomethyl ether acetate or a mixed solvent of two or more kinds including propylene glycol monomethyl ether acetate.

The concentration of the solid content in the composition of the embodiment of the present invention is preferably 1.0% to 10% by mass, more preferably 2.0% to 5.7% by mass, and still more preferably 2.0% to 5.3% by mass. That is, in a case where the composition includes a solvent, a content of the solvent in the composition is preferably adjusted so as to satisfy the suitable range of the concentration of the solid content. Furthermore, the concentration of the solid content is a mass percentage of other resist components excluding the solvent with respect to the total mass of the composition.

By setting the concentration of the solid content in the composition to an appropriate range to attain an appropriate viscosity and improving the coating property or the film-forming property, the film thickness of a resist film (actinic ray-sensitive or radiation-sensitive film) consisting of the composition of the embodiment of the present invention can be adjusted.

<Other Additives>

The composition of the embodiment of the present invention may further include a resin other than those described above, a crosslinking agent, a surfactant, an acid proliferation agent, a dye, a plasticizer, a photosensitizer, a light absorber, an alkali-soluble resin, a dissolution inhibitor, a dissolution accelerator, or the like.

<Preparation Method>

The composition of the embodiment of the present invention is preferably used by dissolving the components in a predetermined organic solvent (preferably the mixed solvent), and filtering the solution through a filter and applying it onto a predetermined support (substrate).

The pore size of a filter for use in filtration through the filter is preferably pore size of 0.1 μm or less, more preferably 0.05 μm or less, and still more preferably 0.03 μm or less. As the filter, a polytetrafluoroethylene-made, polyethylene-made, or nylon-made filter is preferable. In the filtration through a filter as shown in the specification of JP2002-062667A, circulating filtration may be performed or the filtration may be performed by connecting plural kinds of filters in series or in parallel. In addition, the composition may be filtered in plural times. Furthermore, the composition may be subjected to a deaeration treatment or the like before or after filtration through a filter.

<Applications>

The composition of the embodiment of the present invention relates to an actinic ray-sensitive or radiation-sensitive resin composition whose properties change by undergoing a reaction upon irradiation with actinic rays or radiation. More specifically, the composition of the embodiment of the present invention relates to an actinic ray-sensitive or radiation-sensitive resin composition which is used in a step of manufacturing a semiconductor such as an integrated circuit (IC), for manufacture of a circuit board for a liquid crystal, a thermal head, or the like, the manufacture of a mold structure for imprinting, other photofabrication steps, or production of a planographic printing plate or an acid-curable composition. A pattern formed in the present invention can be used in an etching step, an ion implantation step, a bump electrode forming step, a rewiring forming step, a microelectromechanical system (MEMS), or the like.

[Pattern Forming Method and Resist Film]

The present invention also relates to a pattern forming method using the actinic ray-sensitive or radiation-sensitive resin composition. Hereinafter, the pattern forming method of the embodiment of the present invention will be described. Further, the resist film (actinic ray-sensitive or radiation-sensitive film) of the embodiment of the present invention will be described together with the description of the pattern forming method.

The pattern forming method of the embodiment of the present invention has:

(i) a step of forming a resist film (actinic ray-sensitive or radiation-sensitive film) on a support using the above-described actinic ray-sensitive or radiation-sensitive resin composition (resist film forming step (film forming step)), (ii) a step of exposing the resist film (irradiating actinic rays or radiation) (exposing step), and (iii) a step of developing the exposed resist film with a developer (developing step).

The pattern forming method of the embodiment of the present invention is not particularly limited as long as it includes the steps (i) to (iii), and may further include the following steps.

In the pattern forming method of the embodiment of the present invention, the exposing method in the exposing step (ii) may be liquid immersion exposure.

The pattern forming method of the embodiment of the present invention preferably includes a prebaking (PB) step (iv) before the exposing step (ii).

The pattern forming method of the embodiment of the present invention preferably includes a post-exposure baking (PEB) step (v) after the exposing step (ii) and before the developing step (iii).

The pattern forming method of the embodiment of the present invention may include the exposing step (ii) a plurality of times.

The pattern forming method of the embodiment of the present invention may include the prebaking step (iv) a plurality of times.

The pattern forming method of the embodiment of the present invention may include the post-exposure baking step (v) a plurality of times.

In the pattern forming method of the embodiment of the present invention, the above-described resist film forming step (film forming step) (i), exposing step (ii), and developing step (iii) can be performed by a generally known method.

The thickness of the resist film is preferably 110 nm or less, and more preferably 95 nm or less, from the viewpoint of improving resolving power.

In addition, a resist underlayer film (for example, spin on glass (SOG), spin on carbon (SOC), and an antireflection film) may be formed between the resist film and the support, as desired. As a material constituting the resist underlayer film, known organic or inorganic materials can be appropriately used.

A protective film (topcoat) may be formed on the upper layer of the resist film. As the protective film, a known material can be appropriately used. For example, the compositions for forming a protective film disclosed in the specification of US2007/0178407A, the specification of US2008/0085466A, the specification of US2007/0275326A, the specification of US2016/0299432A, the specification of US2013/0244438A, or the specification of WO2016/157988A can be suitably used. The composition for forming a protective film preferably includes the above-described acid diffusion control agent.

A protective film may be formed on the upper layer of the resist film including the above-mentioned hydrophobic resin.

The support is not particularly limited, and a substrate which is generally used in a step of manufacturing a semiconductor such as an IC, and a process for manufacturing a circuit board for a liquid crystal, a thermal head, or the like, and other lithographic processes of photofabrication can be used. Specific examples of the support include an inorganic substrate such as silicon, $SiO_2$, and SiN.

For any of the prebaking step (iv) and the post-exposure baking step (v), the baking temperature is preferably 70° C. to 130° C., and more preferably 80° C. to 120° C.

For any of the prebaking step (iv) and the post-exposure baking step (v), the baking time is preferably 30 to 300 seconds, more preferably 30 to 180 seconds, and still more preferably 30 to 90 seconds.

The baking may be performed using a unit included in an exposure apparatus and a development device, or may also be performed using a hot plate or the like.

A light source wavelength used in the exposing step is not particularly limited, and examples thereof include infrared rays, visible light, ultraviolet rays, far ultraviolet rays, extreme ultraviolet rays (EUV), X-rays, and electron beams. Among those, far ultraviolet rays are preferable, and a wavelength thereof is preferably 250 nm or less, more preferably 220 nm or less, and still more preferably 1 to 200 nm. Specifically, a KrF excimer laser (248 nm), an ArF excimer laser (193 nm), an F2 excimer laser (157 nm), X-rays, EUV (13 nm), or electron beams are preferable, and the KrF excimer laser, the ArF excimer laser, EUV, or the electron beams are preferable.

In the developing step (iii), the developer may be either an alkali developer or a developer including an organic solvent (hereinafter also referred to as an organic developer).

As the alkali developer, a quaternary ammonium salt typified by tetramethylammonium hydroxide is usually used, but in addition to this, an aqueous alkaline solution such as an inorganic alkali, primary to tertiary amines, an alcoholamine, and a cyclic amine can also be used.

Furthermore, the alkali developer may include an appropriate amount of alcohols and/or a surfactant. The alkali concentration of the alkali developer is usually 0.1% to 20% by mass. The pH of the alkali developer is usually 10 to 15.

A time period for performing development the using the alkali developer is usually 10 to 300 seconds.

The alkali concentration, the pH, and the development time using the alkali developer can be appropriately adjusted depending on a pattern formed.

The organic developer is preferably a developer including at least one organic solvent selected from the group consisting of a ketone-based solvent, an ester-based solvent, an alcohol-based solvent, an amide-based solvent, an ether-based solvent, and a hydrocarbon-based solvent.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butyrate, methyl 2-hydroxyisobutyrate, isoamyl acetate, isobutyl isobutyrate, and butyl propionate.

As the alcohol-based solvent, the amide-based solvent, the ether-based solvent, and the hydrocarbon-based solvent, the solvents disclosed in paragraphs [0715] to [0718] of the specification of US2016/0070167A1 can be used.

A plurality of the solvents may be mixed or the solvent may be used in admixture with a solvent other than those described above or water. The moisture content in the entire developer is preferably less than 50% by mass, more preferably less than 20% by mass, and still more preferably less than 10% by mass, and particularly preferably, moisture is not substantially included.

The content of the organic solvent with respect to the organic developer is preferably 50% to 100% by mass, more preferably 80% to 100% by mass, still more preferably 90% to 100% by mass, and particularly preferably 95% to 100% by mass, with respect to the total amount of the developer.

The developer may include an appropriate amount of a known surfactant, as desired.

The content of the surfactant is usually 0.001% to 5% by mass, preferably 0.005% to 2% by mass, and still more preferably 0.01% to 0.5% by mass, with respect to the total amount of the developer.

The organic developer may include the acid diffusion control agent.

Examples of the developing method include a method in which a substrate is dipped in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), and a method in which a developer is continuously jetted onto a substrate spun at a constant rate while scanning a developer jetting nozzle at a constant rate (a dynamic dispense method).

A combination of a step of performing development using an aqueous alkali solution (an alkali developing step) and a step of performing development using a developer including an organic solvent (an organic solvent developing step) may be used. Thus, a finer pattern can be formed since a pattern can be formed by keeping only a region with an intermediate exposure intensity from not being dissolved.

It is preferable that the method includes a step of performing washing using a rinsing liquid (a rinsing step) after the developing step (iii).

As the rinsing liquid used in the rinsing step after the developing step with an alkali developer, for example, pure water can be used. The pure water may include an appropriate amount of a surfactant. Moreover, after the developing step or the rinsing step, a treatment for removing the developer or the rinsing liquid adhering on a pattern by a supercritical fluid may be added. In addition, after the rinsing treatment or the treatment using a supercritical fluid, a heating treatment for removing moisture remaining in the pattern may be performed.

The rinsing liquid used in the rinsing step after the developing step with a developer including an organic solvent is not particularly limited as long as the rinsing liquid does not dissolve the pattern, and a solution including a common organic solvent can be used. As the rinsing liquid, a rinsing liquid including at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent include the same solvents as those described for the developer including an organic solvent.

As the rinsing liquid used in the rinsing step in this case, a rinsing liquid including a monohydric alcohol is more preferable.

Here, examples of the monohydric alcohol used in the rinsing step include linear, branched, or cyclic monohydric alcohols. Specific examples thereof include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol, and methyl isobutyl carbinol.

The monohydric alcohol preferably has 5 or more carbon atoms and examples thereof include 1-hexanol, 2-hexanol, 4-methyl-2-pentanol, 1-pentanol, 3-methyl-1-butanol, and methyl isobutyl carbinol.

The respective components in a plural number may be mixed or the components may also be used in admixture with an organic solvent other than the solvents.

A moisture content in the rinsing liquid used in the rinsing step after the developing step using the developer including the organic solvent is preferably 10% by mass or less, more preferably 5% by mass or less, and still more preferably 3% by mass or less. By setting the moisture content to 10% by mass or less, good development characteristics are obtained.

The rinsing liquid after the developing step using the developer including the organic solvent may include an appropriate amount of the surfactant.

In the rinsing step, the developed substrate is subjected to a washing treatment using a rinsing liquid. A method for the washing treatment method is not particularly limited, but examples thereof include a method in which a rinsing liquid is continuously jetted on a substrate rotated at a constant rate (a rotation application method), a method in which a substrate is dipped in a tank filled with a rinsing liquid for a certain period of time (a dip method), and a method in which a rinsing liquid is sprayed on a substrate surface (a spray method). Among those, a method in which a washing treatment is carried out using the rotation application method, and a substrate is rotated at a rotation speed of 2,000 to 4,000 rpm after washing, thereby removing the rinsing liquid from the substrate is preferable. Furthermore, it is also preferable that the method includes a baking step after the rinsing step (postbaking). The developer and the rinsing liquid remaining between and inside the patterns are removed by the baking step. In the baking step after the rinsing step, the baking temperature is usually 40° C. to 160° C., and preferably 70° C. to 95° C., and the baking time is typically 10 seconds to 3 minutes, and preferably 30 seconds to 90 seconds.

It is preferable that various materials (for example, a resist solvent, a developer, a rinsing liquid, a composition for forming an antireflection film, and a composition for forming a topcoat) used in the actinic ray-sensitive or radiation-sensitive resin composition of the embodiment of the present invention, and the pattern forming method of the embodiment of the present invention do not include impurities such as metal components, isomers, and residual monomers. The content of the impurities included in these materials is preferably 1 ppm by mass or less, more preferably 100 ppt by mass or less, and still more preferably 10 ppt by mass or less, and particularly preferably, the impurities are not substantially included (no higher than a detection limit of a measurement device).

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a polytetrafluoroethylene-made, polyethylene-made, or nylon-made filter is preferable. As the filter, a filter which has been washed with an organic solvent in advance may be used. In the step of filtration using a filter, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step. As the filter, a filter having a reduced amount of eluates as disclosed in the specification of JP2016-201426A is preferable.

In addition to the filtration using a filter, removal of impurities using an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used. Examples of the metal adsorbing material include those disclosed of the specification of JP2016-206500A.

In addition, as a method for reducing the impurities such as metals included in the various materials, metal content selects the less material as a raw material constituting the various materials, performing filtering using a filter of the raw material constituting the various materials, equipment the inner and a method such as performing distillation under conditions suppressing as much where available equal to contamination is lined with TEFLON (registered trademark). Preferred conditions in the filtering using a filter to be performed on the raw material constituting the various materials are the same as the above-described conditions.

In addition, it is also preferable that the inside of an apparatus used in a step of producing raw materials (a resin, a photoacid generator, and the like) for the composition (a step of synthesizing raw materials, and the like) may be partially or wholly subjected to a glass lining treatment in order to reduce the content of metal impurities of the resist composition to a small amount (for example, a mass ppt order).

In order to prevent impurities from being incorporated, it is preferable that various materials are stored in the container described in the specification of US2015/0227049A, the specification of JP2015-123351A, or the like.

A method for improving the surface roughness of a pattern may be applied to a pattern formed by the pattern forming method of the embodiment of the present invention. Examples of the method for improving the surface roughness of a pattern include the method of treating a pattern by plasma of a hydrogen-containing gas, as disclosed in the specification of US2015/0104957A. In addition, known methods as described in the specification of JP2004-235468A, the specification of US2010/0020297A, and Proc. of SPIE Vol. 8328 83280N-1 "EUV Resist Curing Technique for LWR Reduction and Etch Selectivity Enhancement" may be applied.

In addition, a pattern formed by the method can be used as a core material (core) of the spacer process disclosed in, for example, the specification of JP1991-270227A (JP-H03-270227A) and the specification of US2013/0209941A.

[Method for Manufacturing Electronic Device]

Moreover, the present invention further relates to a method for manufacturing an electronic device, the method including the above-described pattern forming method. The electronic device manufactured by the method for manufacturing an electronic device of an embodiment of the present invention is suitably mounted on electric or electronic equipment (for example, home electronics, office automation (OA)-related equipment, media-related equipment, optical equipment, and telecommunication equipment).

EXAMPLES

Hereinbelow, the present invention will be described in more detail with reference to Examples. The materials, the amounts of materials used, the proportions, the treatment details, the treatment procedure, and the like shown in the Examples below may be modified as appropriate as long as the modifications do not depart from the spirit of the present invention. Therefore, the scope of the present invention should not be construed as being limited to the Examples shown below.

[Actinic Ray-Sensitive or Radiation-Sensitive Resin Composition]

[Components]

The components included in the actinic ray-sensitive or radiation-sensitive resin composition (hereinafter also referred to as the "composition") used in Examples or Comparative Examples are shown below.

<Resin A>

A resin A used in the production of the composition is shown below.

In the following formula, * represents a bonding position.

The description given below the name of each resin A indicates, from the top, the compositional ratio (molar ratio), the weight-average molecular weight, and the dispersity in this order of each repeating unit.

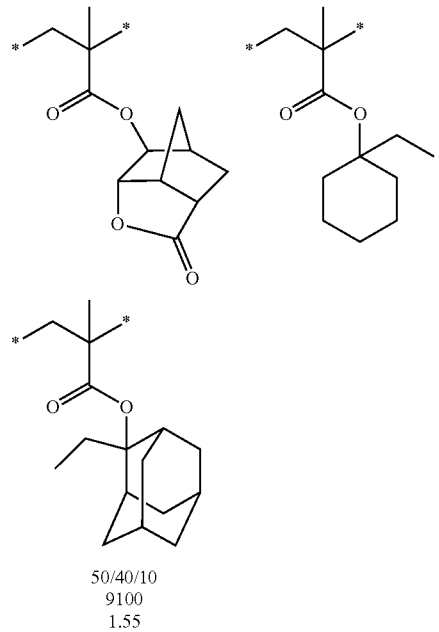

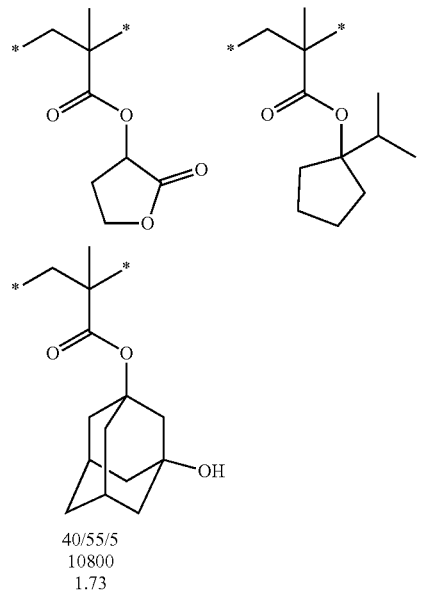

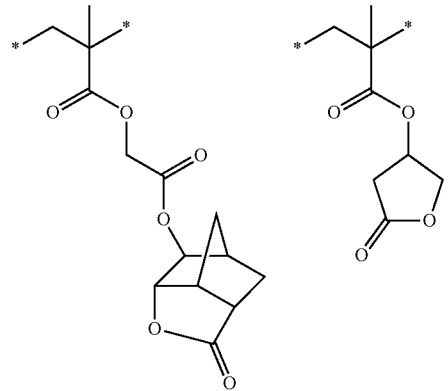

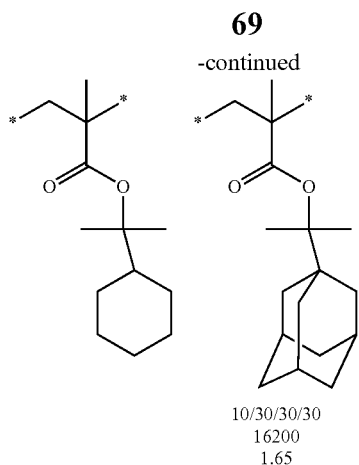

10/30/30/30
16200
1.65

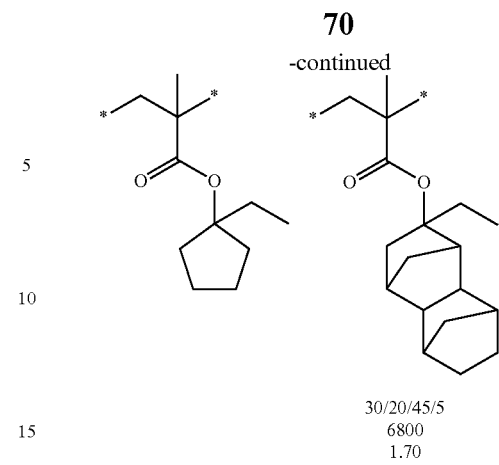

30/20/45/5
6800
1.70

Pol-4

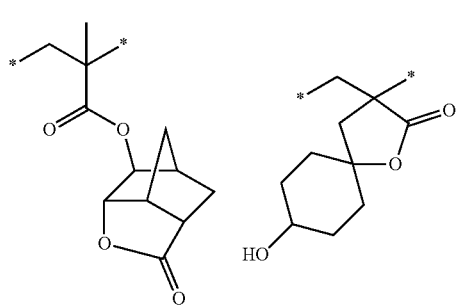

<Photoacid Generator>

The photoacid generator used for the preparation of the composition is shown below.

Furthermore, the following B1-1 to B1-7 are specific photoacid generators, and the following B2-1 to B2-4 are other photoacid generators which do not correspond to the specific photoacid generators.

The numerical value given together with each photoacid generator represents the pka of an acid generated from the photoacid generator.

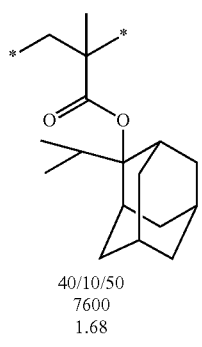

40/10/50
7600
1.68

Pol-5

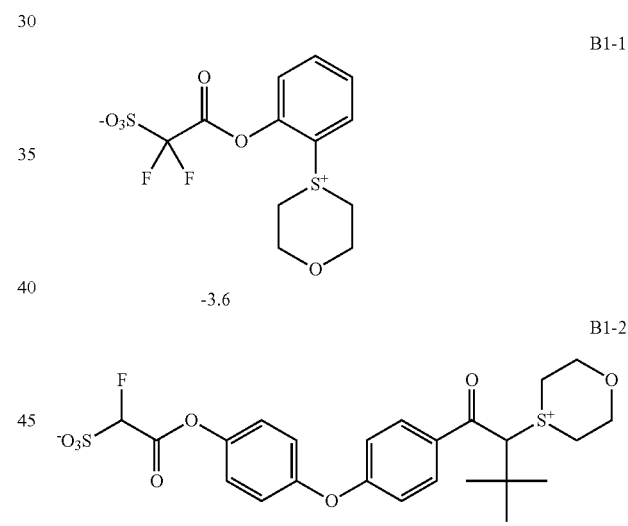

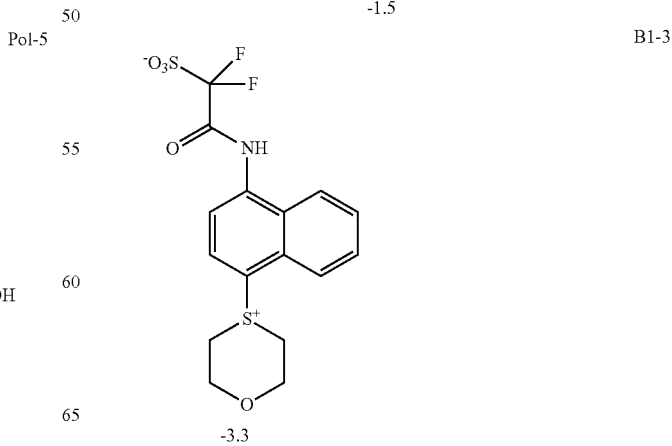

B1-4
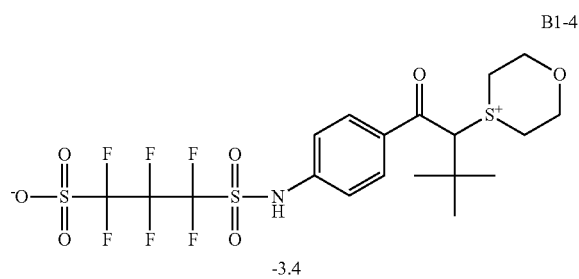
-3.4
B1-5
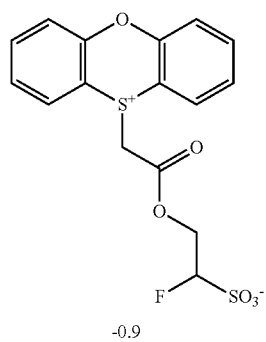
-0.9
B1-6
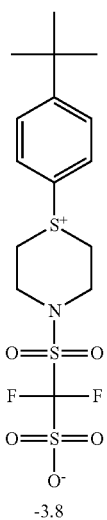
-3.8
B1-7
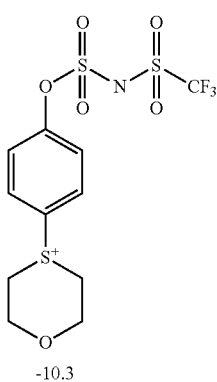
-10.3
B2-1
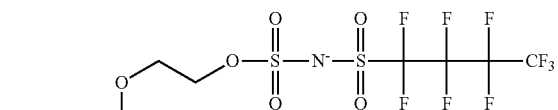
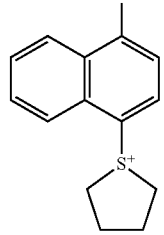
-6.7
B2-2
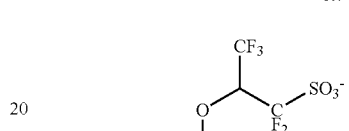
-3.1
B2-3
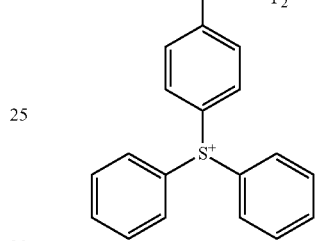
-2.0
B2-4
-3.3
<Acid Diffusion Control Agent>
The acid diffusion control agent used for the preparation of the composition is shown below.
The numerical value given together with each acid diffusion control agent represents the pka of an acid generated by the acid diffusion control agent in a case where the acid diffusion control agent generates the acid.

D-1
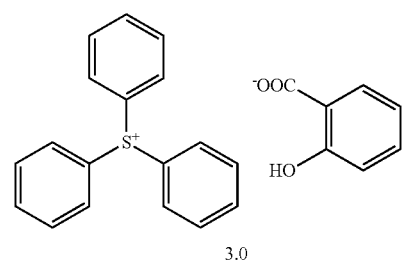

D-2
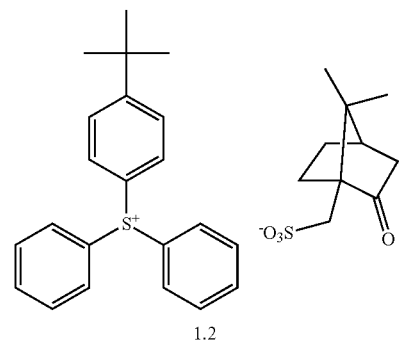

D-3
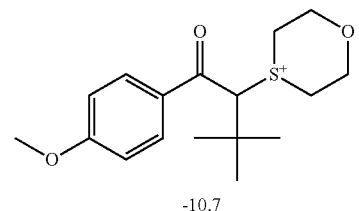

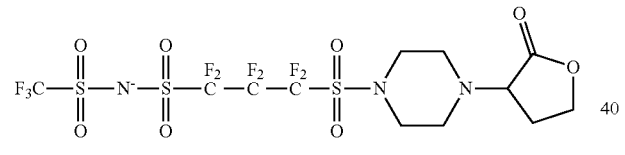

D-4
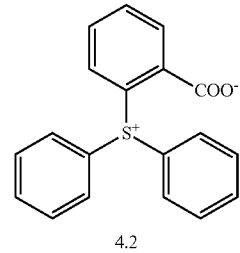

D-5

D-6
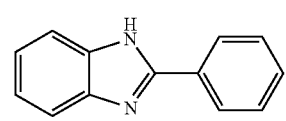

D-7
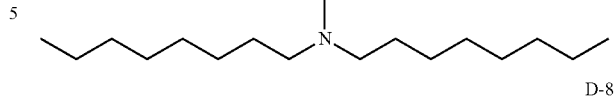

D-8
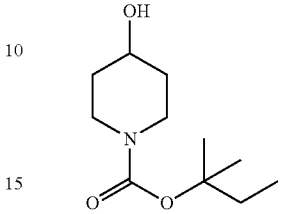

<Hydrophobic Resin>

The hydrophobic resins used to prepare the composition are shown below.

In the following formula, * represents a bonding position.

The description given together with the name of each hydrophobic resin means, in order from the top, the compositional ratio (molar ratio), the weight-average molecular weight, and the dispersity of each repeating unit.

F-1
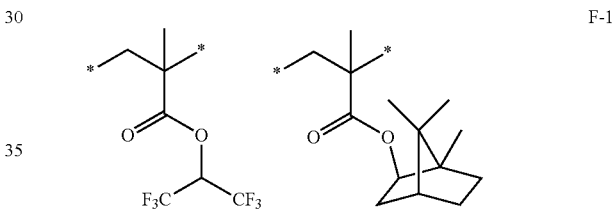

40/55/5
5500
1.60

F-2
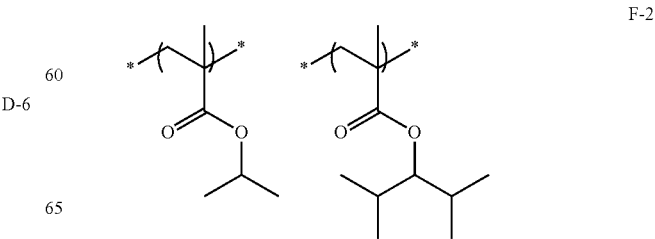

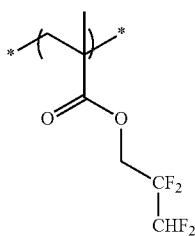

30/65/5
7200
1.61

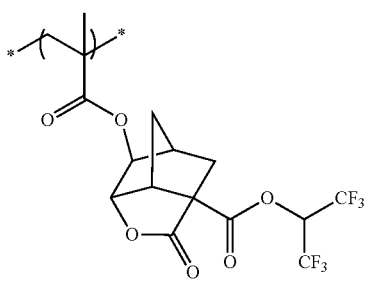

35/60/5
8000
1.70

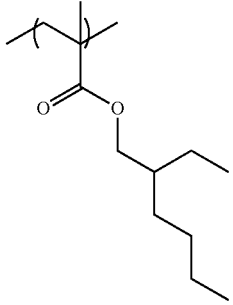

55/45
6300
1.68

F-5

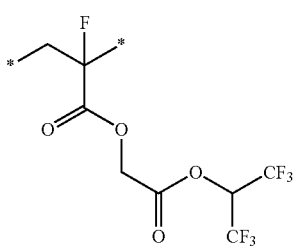

F-3

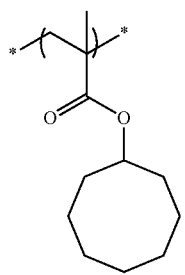

40/50/5/5
15900
1.63

F-6

70/30
10200
1.65

F-7

30/70
6900
1.63

F-4

<Solvent>

The solvents used to prepare the composition are shown below.

G-1; Propylene glycol monomethyl ether acetate (PG-MEA)
G-2; Cyclohexanone
G-3; Propylene glycol monomethyl ether (PGME)
G-4; γ-Butyrolactone
G-5; Ethyl lactate

[Preparation of Composition]

Each component was dissolved in a solvent according to the formulation shown in the table shown in the latter part, and a solution having a concentration of the solid content of 3.8% by mass was prepared for each. Then, the obtained solution was filtered through a polyethylene filter having a pore size of 0.03 μm to prepare an actinic ray-sensitive or radiation-sensitive resin composition (composition).

[Evaluation]
<Pattern Formation>
<<Formation of Resist Film>>

A composition for forming an organic antireflection film ARC29SR (manufactured by Nissan Chemical Industries, Ltd.) was applied onto a silicon wafer and baked at 205° C.

for 60 seconds to form an antireflection film having a film thickness of 95 nm. Each composition prepared by the formulation shown in the table shown in the latter section was applied thereonto and baked (PB: prebaking) for 60 seconds to form a resist film having a film thickness of 90 nm.

(Exposure to Development)

The obtained silicon wafer was subjected to pattern exposure by using an ArF liquid immersion exposure apparatus (NA 1.20) through a binary mask with a 1:1 line-and-space pattern having a line width of 44 nm. Thereafter, the silicon wafer was baked (PEB; post-exposure baking) for 60 seconds and developed for 30 seconds with a negative tone developer (butyl acetate). Then, the silicon wafer was dried under rotation speed at 4,000 rpm for 30 seconds to obtain a line-and-space pattern of 44 nm (1:1).

The conditions (temperature (° C.)) of PE and PEB for pattern formation are shown in the following table with regard to each of Examples and Comparative Examples.

<LWR Performance>

The obtained 1:1 line-and-space pattern with a line width of 44 nm was observed. In the observation of the pattern, the pattern was observed from the top with a critical dimension scanning electron microscope (SEM (S-9380II manufactured by Hitachi High Technologies Corporation)).

The line width at 50 points was measured at equal intervals in the range of 2 μm in the longitudinal direction of the line pattern, and 3σ (nm) was calculated from the standard deviation thereof. A smaller value thereof indicates better performance.

<Pattern Collapse Suppressing Property>

In the above-mentioned pattern formation, the mask used was changed to perform pattern formation. Further, in a case where an exposure dose for reproducing a mask pattern with a pitch of 90 nm and a space width of 35 nm was set as an optimum exposure dose and the line width of a line pattern formed by further changing the exposure dose from the optimum exposure amount was reduced, a pattern collapse suppressing property was defined as a critical maximum space width (nm) at which the pattern was resolved without collapse. A larger value thereof indicates that a finer pattern is resolved without collapse, and the pattern collapse suppressing property is excellent and the resolving power is high.

[Results]

The formulation of the composition and the results of the evaluations performed using these compositions are shown in the following table.

In the column of "Solid content", the number described below each component name indicates the content (% by mass) of each component with respect to the total solid content in the composition.

The description of the numerical values in parentheses in the column of "Solvent" indicates the mixing ratio (volume ratio) of the solvent contained in each composition.

The column of "Type of anionic group" shows which of General Formulae (b1-1) to (b1-3) the anionic group of the specific photoacid generator included in each composition is represented by.

The column of "Formula ZI-3, Formula ZI-4" shows whether or not the specific photoacid generator included in each composition corresponds to the compound represented by General Formula (ZI-3) or the compound represented by General Formula (ZI-4). A case where the specific photoacid generator corresponds to the compound is cited as A, and a case where the specific photoacid generator does not correspond to the compound is cited as B.

The column of "Acid generation and acid diffusion control agent" shows whether or not the acid diffusion control agent included in each composition corresponds to a basic compound whose basicity is reduced or lost upon irradiation with actinic rays or radiation. A case where the specific photoacid generator corresponds to the compound is cited as A, and a case where the specific photoacid generator does not correspond to the compound is cited as B.

The column of "Formula (c-1)" shows whether or not an acid thus generated corresponds to an acid represented by General Formula (c-1) in a case where in a case where the acid diffusion control agent included in each composition corresponds to a compound which generates an acid upon irradiation with actinic rays or radiation. A case where the specific photoacid generator corresponds to the compound is cited as A, and a case where the specific photoacid generator does not correspond to the compound is cited as B.

TABLE 1

| | | Composition | | | | | | | |
|---|---|---|---|---|---|---|---|---|---|
| | | Solid content | | | | | | Pattern formation | |
| | | | Photoacid | | Acid diffusion | | Hydrophobic | | | |
| | Type of composition | Resin/ content | generator/ content | | control agent/ content | | resin/ content | Solvent | PB (° C.) | PEB (° C.) |
| Example 1 | R-01 | Pol-1 88.0 | B1-1 7.0 | | D-1 3.0 | | F-1 2.0 | G-1/G-2 (60/40) | 90 | 100 |
| Example 2 | R-02 | Pol-2 84.0 | B1-2 5.5 | B2-3 2.5 | D-2 4.0 | | F-2 4.0 | G-1/G-3 (70/30) | 100 | 90 |
| Example 3 | R-03 | Pol-3 83.0 | B1-3 10.5 | | D-3 4.5 | | F-3 2.0 | G-1/G-4 (95/5) | 95 | 85 |
| Example 4 | R-04 | Pol-4 86.5 | B1-4 10.0 | | D-4 2.0 | D-8 0.5 | F-4 1.0 | G-1/G-5 (90/10) | 110 | 95 |
| Example 5 | R-05 | Pol-5 83.2 | B1-5 13.5 | | D-5 2.5 | | F-5 0.8 | G-1/G-3 (70/30) | 115 | 100 |
| Example 6 | R-06 | Pol-5 85.3 | B1-6 8.5 | B2-4 4.5 | D-6 0.5 | | F-6 1.2 | G-1/G-3 (70/30) | 100 | 90 |
| Example 7 | R-07 | Pol-5 85.3 | B1-7 12.3 | | D-7 0.4 | | F-7 2.0 | G-1/G-3 (70/30) | 100 | 85 |

TABLE 1-continued

| | | | | | | | | |
|---|---|---|---|---|---|---|---|---|
| Comparative Example 1 | R-09 | Pol-5 86.0 | B2-1 9.0 | D-2 3.0 | F-1 2.0 | G-1/G-3 (70/30) | 90 | 95 |
| Comparative Example 2 | R-10 | Pol-5 86.5 | B2-2 8.5 | D-2 3.0 | F-1 2.0 | G-1/G-3 (70/30) | 90 | 100 |

| | Composition characteristics | | | | Evaluation | |
|---|---|---|---|---|---|---|
| | Type of anionic group | Formula ZI-3, Formula ZI-4 | Acid generation and acid diffusion control agent | Formula c-1 | LWR performance (nm) | Pattern collapse suppressing property (nm) |
| Example 1 | b1-1 | A | A | B | 3.2 | 52.2 |
| Example 2 | b1-1 | A | A | B | 3.1 | 53.6 |
| Example 3 | b1-1 | A | A | A | 3.0 | 53.9 |
| Example 4 | b1-1 | A | A | B | 3.1 | 51.3 |
| Example 5 | b1-1 | B | A | B | 3.3 | 50.3 |
| Example 6 | b1-1 | A | B | — | 3.6 | 47.5 |
| Example 7 | b1-2 | A | B | — | 3.8 | 49.0 |
| Comparative Example 1 | — | — | — | — | 4.6 | 42.5 |
| Comparative Example 2 | — | — | — | — | 4.2 | 39.0 |

From the results shown in the table, it was confirmed that with the composition of the embodiment of the present invention, a pattern having an excellent pattern collapse suppressing property and excellent LWR performance can be obtained.

In addition, it was confirmed that in a case where the specific photoacid generator has the anionic group represented by General Formula (b1-1) as an anionic group, a pattern having more excellent LWR performance can be obtained (comparison of Example 7 vs. other Examples).

It was confirmed that in a case where the composition includes a basic compound whose basicity is reduced or lost upon irradiation with actinic rays or radiation, a pattern having a more excellent pattern collapse suppressing property and more excellent LWR performance can be obtained (comparison of Examples 1 to 5 vs. Examples 6 and 7).

It was confirmed that in a case where the composition includes the basic compound whose basicity is reduced or lost upon irradiation with actinic rays or radiation, in the compound has an anion represented by General Formula (c-1), a pattern having a more excellent pattern collapse suppressing property and more excellent LWR performance can be obtained (the results of Example 3).

It was confirmed that in a case where the specific photoacid generator is the compound represented by General Formula (ZI-3) or the compound represented by General Formula (ZI-4), a pattern having a more excellent pattern collapse suppressing property and more excellent LWR performance can be obtained (comparison of Example 5 vs. Examples 1 to 4 (comparison between the compositions including the basic compound whose basicity is reduced or lost upon irradiation with actinic rays or radiation)).

What is claimed is:

1. An actinic ray-sensitive or radiation-sensitive resin composition comprising:
   a resin whose solubility in a developer is changed by the action of an acid; and
   a photoacid generator represented by General Formula (b1),
   wherein the photoacid generator represented by General Formula (b1) is a compound that generates an acid having a pka of 1.0 or less upon irradiation with actinic rays or radiation,

in General Formula (b1), $R_1$ represents a substituent, $R_2$ represents a group forming a having at least one heteroatom other than $S^+$, which may have a substituent, together with $S^+$, and an aromatic ring group is not disposed at at least one of a position bonded to $S^+$ in $R_1$ and two positions bonded to $S^+$ in $R_2$, provided that the substituent represented by $R_1$ has an anionic group which is a group having a sulfonate anion group or the group represented by $R_2$ has an anionic group which is a group having a sulfonate anion group.

2. The actinic ray-sensitive or radiation-sensitive resin composition according to claim 1,
   wherein the anionic group is a group represented by General Formula (b1-1),

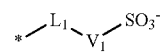

in General Formula (b1-1), $L_1$ represents a single bond or a divalent linking group, $V_1$ represents a single bond or a hydrocarbon group which may have a fluorine atom, and

* represents a bonding position.

3. The actinic ray-sensitive or radiation-sensitive resin composition according to claim 2,
   wherein the photoacid generator represented by General Formula (b1) is a compound represented by General Formula (ZI-3) or a compound represented by General Formula (ZI-4), (ZI-3)

[Chemical structure: benzene ring with R1c, R2c, R3c, R4c, R5c substituents, connected to C(=O)-C(R6c)(R7c)-S+-R2 (ring)]

in General Formula (ZI-3),
$R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, an arylthio group, or an anionic group,
$R_{6c}$ and $R_{7c}$ each independently represent a hydrogen atom, an alkyl group, a cycloalkyl group, a halogen atom, a cyano group, an aryl group, or an anionic group, and
$R_2$ represents a group forming a heterocycle having at least one heteroatom other than $S^+$, which may have a substituent, together with $S^+$,
provided that any one of $R_{1c}$, . . . , or $R_{7c}$, is an anionic group which is the group represented by General Formula (b1-1), or $R_2$ is a group having an anionic group which is the group represented by General Formula (b1-1), (ZI-4)

[Chemical structure: naphthalene-like ring system with R13, (R14)r substituents, S+ with R2 forming ring, Z⁻ counterion]

in General Formula (ZI-4),
l represents an integer of 0 to 2,
r represents an integer of 0 to 8,
$R_{13}$ represents a group having a hydrogen atom, a fluorine atom, a hydroxyl group, an alkyl group, an alkoxy group, an alkoxycarbonyl group, a cycloalkyl group, or an anionic group,
$R_{14}$ represents a hydroxyl group, an alkyl group, an alkoxy group, an alkoxycarbonyl group, an alkylcarbonyl group, an alkylsulfonyl group, a cycloalkylsulfonyl group, a group having a cycloalkyl group, or an anionic group,
$R_2$ represents a group forming a heterocycle having at least one heteroatom other than $S^+$, which may have a substituent, together with $S^+$, and
an aromatic ring group is not disposed at at least one of the two positions bonded to $S^+$ in $R_2$,
provided that any one of $R_{13}$ and any one of $R_{14}$'s which may be present in a plural number are each an anionic group which is the group represented by General Formula (b1-1), or $R_2$ is a group having an anionic group which is the group represented by General Formula (b1-1).

4. The actinic ray-sensitive or radiation-sensitive resin composition according to claim 1,
wherein the photoacid generator represented by General Formula (b1) is a compound represented by General Formula (ZI-3) or a compound represented by General Formula (ZI-4), (ZI-3)

[Chemical structure: benzene ring with R1c, R2c, R3c, R4c, R5c substituents, connected to C(=O)-C(R6c)(R7c)-S+-R2 (ring)]

in General Formula (ZI-3),
$R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, an arylthio group, or an anionic group,
$R_{6c}$ and $R_{7c}$ each independently represent a hydrogen atom, an alkyl group, a cycloalkyl group, a halogen atom, a cyano group, an aryl group, or an anionic group, and
$R_2$ represents a group forming a heterocycle having at least one heteroatom other than $S^+$, which may have a substituent, together with $S^+$,
provided that any one of $R_{1c}$, . . . , or $R_{7c}$ is an anionic group which is a group having a sulfonate anion group, or $R_2$ is a group having an anionic group which is a group having a sulfonate anion group, (ZI-4)

[Chemical structure: naphthalene-like ring system with R13, (R14)r substituents, S+ with R2 forming ring, Z⁻ counterion]

in General Formula (ZI-4),
l represents an integer of 0 to 2,
r represents an integer of 0 to 8,
$R_{13}$ represents a group having a hydrogen atom, a fluorine atom, a hydroxyl group, an alkyl group, an alkoxy group, an alkoxycarbonyl group, a cycloalkyl group, or an anionic group,
$R_{14}$ represents a hydroxyl group, an alkyl group, an alkoxy group, an alkoxycarbonyl group, an alkylcarbonyl group, an alkylsulfonyl group, a cycloalkylsulfonyl group, a group having a cycloalkyl group, or an anionic group,
$R_2$ represents a group forming a heterocycle having at least one heteroatom other than $S^+$, which may have a substituent, together with $S^+$, and
an aromatic ring group is not disposed at at least one of the two positions bonded to $S^+$ in $R_2$, provided that any one of $R_{13}$ and any one of $R_{14}$'s which may be present in a plural number are each an anionic group which is a group having a sulfonate anion group, or $R_2$ is a group having an anionic group which is a group having a sulfonate anion group.

5. The actinic ray-sensitive or radiation-sensitive resin composition according to claim 1, further comprising an acid diffusion control agent.

6. The actinic ray-sensitive or radiation-sensitive resin composition according to claim 5,
wherein the acid diffusion control agent is a basic compound whose basicity is reduced or lost upon irradiation with actinic rays or radiation, with the compound being different from the photoacid generator represented by General Formula (b1).

7. The actinic ray-sensitive or radiation-sensitive resin composition according to claim 6,
wherein the basic compound whose basicity is reduced or lost upon irradiation with actinic rays or radiation is a compound having an anion represented by General Formula (c-1),

  (c-1)

in General Formula (c-1),
Q represents $—SO_3^-$, $—CO_2^-$, or $—W_1—N^-—W_2R_f$,
$W_1$ and $W_2$ each independently represent $—SO_2—$ or $—CO—$,
$R_f$ represents an alkyl group which may have a substituent, a cycloalkyl group which may have a substituent, or an aryl group which may have a substituent,
A represents a single bond or a divalent linking group,
X represents a single bond, $—SO_2—$, or $—CO—$,
B represents a single bond, an oxygen atom, or $—N(R_x)R_y—$,
$R_x$ represents a hydrogen atom or an organic group,
$R_y$ represents a single bond or a divalent organic group,
R represents a monovalent organic group having a proton-accepting functional group, and
$R_x$ may be bonded to $R_y$ to form a ring, and may be bonded to R to form a ring.

8. The actinic ray-sensitive or radiation-sensitive resin composition according to claim 6,
wherein a pka of an acid generated by the basic compound whose basicity is reduced or lost upon irradiation with actinic rays or radiation is more than 1.0.

9. A resist film formed using the actinic ray-sensitive or radiation-sensitive resin composition according to claim 1.

10. A pattern forming method comprising:
a step of forming a resist film using the actinic ray-sensitive or radiation-sensitive resin composition according to claim 1 on a support;
a step of exposing the resist film; and
a step of developing the exposed resist film using a developer.

11. A method for manufacturing an electronic device, comprising the pattern forming method according to claim 10.

12. A resist film formed using the actinic ray-sensitive or radiation-sensitive resin composition according to claim 2.

13. A pattern forming method comprising:
a step of forming a resist film using the actinic ray-sensitive or radiation-sensitive resin composition according to claim 2 on a support;
a step of exposing the resist film; and
a step of developing the exposed resist film using a developer.

14. A method for manufacturing an electronic device, comprising the pattern forming method according to claim 13.

15. A resist film formed using the actinic ray-sensitive or radiation-sensitive resin composition according to claim 4.

* * * * *